(12) United States Patent
Lange et al.

(10) Patent No.: US 7,738,089 B2
(45) Date of Patent: Jun. 15, 2010

(54) METHODS AND SYSTEMS FOR INSPECTION OF A SPECIMEN USING DIFFERENT INSPECTION PARAMETERS

(75) Inventors: Steve R. Lange, Alamo, VA (US); Paul Frank Marella, San Jose, CA (US); Nat Ceglio, Pleasanton, CA (US); Shiow-Hwei Hwang, Livermore, CA (US); Tao-Yi Fu, Fremont, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 685 days.

(21) Appl. No.: 10/933,873

(22) Filed: Sep. 3, 2004

(65) Prior Publication Data

US 2005/0052643 A1    Mar. 10, 2005

Related U.S. Application Data

(60) Provisional application No. 60/500,174, filed on Sep. 4, 2003.

(51) Int. Cl.
*G01N 21/00* (2006.01)
(52) U.S. Cl. .................................. 356/237.1
(58) Field of Classification Search ............. 356/237.1, 356/237.2–237.6; 365/225.5, 230.02; 370/464; 711/156
See application file for complete search history.

(56) References Cited

U.S. PATENT DOCUMENTS

| | | | |
|---|---|---|---|
| 3,877,814 A | * | 4/1975 | Hess et al. .................. 356/613 |
| 4,498,772 A | | 2/1985 | Jastrzebski et al. |
| 4,877,326 A | | 10/1989 | Chadwick et al. |
| 4,933,567 A | * | 6/1990 | Silva et al. ............. 250/559.09 |
| 5,179,422 A | | 1/1993 | Peterson |

(Continued)

FOREIGN PATENT DOCUMENTS

WO    WO 2001/40145    6/2001

(Continued)

OTHER PUBLICATIONS

International Search Report, PCT/US2004/029189, mailed Feb. 9, 2005.

(Continued)

*Primary Examiner*—Tarifur R. Chowdhury
*Assistant Examiner*—Isiaka O Akanbi
(74) *Attorney, Agent, or Firm*—Ann Marie Mewherter

(57) ABSTRACT

Methods and systems for inspection of a specimen using different parameters are provided. One computer-implemented method includes determining optimal parameters for inspection based on selected defects. This method also includes setting parameters of an inspection system at the optimal parameters prior to inspection. Another method for inspecting a specimen includes illuminating the specimen with light having a wavelength below about 350 nm and with light having a wavelength above about 350 nm. The method also includes processing signals representative of light collected from the specimen to detect defects or process variations on the specimen. One system configured to inspect a specimen includes a first optical subsystem coupled to a broadband light source and a second optical subsystem coupled to a laser. The system also includes a third optical subsystem configured to couple light from the first and second optical subsystems to an objective, which focuses the light onto the specimen.

16 Claims, 12 Drawing Sheets

U.S. PATENT DOCUMENTS

| | | | |
|---|---|---|---|
| 5,235,400 A * | 8/1993 | Terasawa et al. | 356/237.5 |
| 5,293,538 A | 3/1994 | Iwata et al. | |
| 5,345,514 A * | 9/1994 | Mahdavieh et al. | 382/152 |
| 5,744,381 A * | 4/1998 | Tabata et al. | 438/16 |
| 5,825,498 A | 10/1998 | Nuttall et al. | |
| 5,936,726 A | 8/1999 | Takeda et al. | |
| 6,104,481 A | 8/2000 | Sekine et al. | |
| 6,157,444 A | 12/2000 | Tomita et al. | |
| 6,266,137 B1 | 7/2001 | Morinaga | |
| 6,392,791 B1 | 5/2002 | Fork et al. | |
| 6,392,793 B1 | 5/2002 | Chuang et al. | |
| 6,538,725 B2 * | 3/2003 | Potyrailo et al. | 356/32 |
| 6,608,321 B1 * | 8/2003 | La Fontaine et al. | 250/559.44 |
| 6,816,249 B2 * | 11/2004 | Fairley et al. | 356/237.1 |
| 6,937,754 B1 * | 8/2005 | Eguchi | 382/145 |
| 7,110,106 B2 * | 9/2006 | Xu et al. | 356/237.5 |
| 7,352,456 B2 | 4/2008 | Lange | |
| 2002/0041374 A1 | 4/2002 | Ohshima et al. | |
| 2002/0089664 A1 * | 7/2002 | Shibata et al. | 356/237.2 |
| 2002/0107660 A1 | 8/2002 | Nikoonahad et al. | |
| 2002/0113234 A1 * | 8/2002 | Okuda et al. | 257/48 |
| 2002/0131052 A1 * | 9/2002 | Emery | 356/511 |
| 2002/0154303 A1 * | 10/2002 | Maeda et al. | 356/394 |
| 2002/0171825 A1 * | 11/2002 | Krantz et al. | 356/237.1 |
| 2003/0008448 A1 | 1/2003 | Kafka et al. | |
| 2003/0025904 A1 * | 2/2003 | Sakai et al. | 356/237.2 |
| 2003/0218741 A1 * | 11/2003 | Guetta | 356/237.1 |
| 2004/0201837 A1 | 10/2004 | Lange | |

FOREIGN PATENT DOCUMENTS

| | | |
|---|---|---|
| WO | 2002/025708 | 3/2002 |
| WO | 2004/092716 | 10/2004 |

OTHER PUBLICATIONS

"The New Wave in Light Technology," © 2001 Wavien, Inc., 4 pages.

"Axicon lenses," Optics.org product release, Feb. 2003, 2 pages.

"Polarization Recovery Light Pipes for Projection Display Applications," © 2002 Optical Coating Laboratory, Inc., 4 pages.

Patent Abstracts of Japan, publication No. 04026845, published Jan. 1992.

International Search Report for PCT/US2004/010324, mailed Sep. 10, 2004.

\* cited by examiner

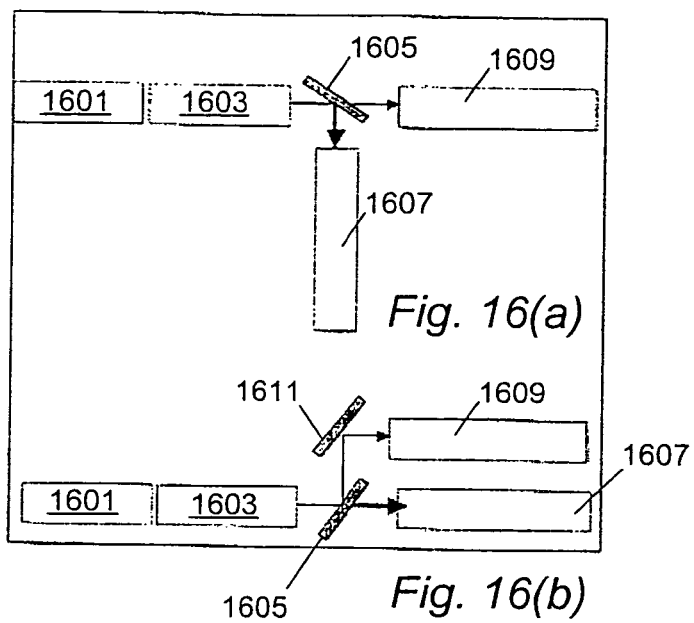
Fig. 16(a)
Fig. 16(b)
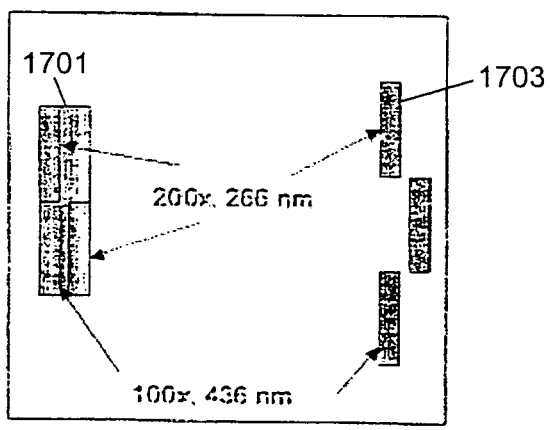
Fig. 17
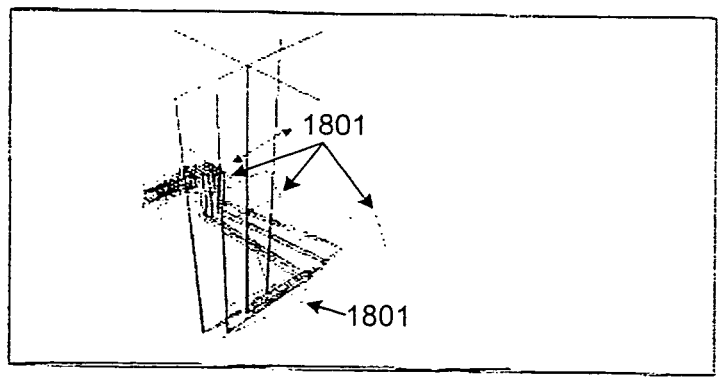
Fig. 18

METHODS AND SYSTEMS FOR INSPECTION OF A SPECIMEN USING DIFFERENT INSPECTION PARAMETERS

PRIORITY CLAIM

This application claims priority to U.S. Provisional Application No. 60/500,174 entitled "Methods and Systems for Inspection of a Specimen Using Different Inspection Parameters," filed Sep. 4, 2003, which is incorporated by reference as if fully set forth herein.

STATEMENT REGARDING FEDERALLY SPONSORED RESEARCH OR DEVELOPMENT

The United States Government may have certain rights to portions of the inventions described herein as provided for by the terms of Cooperative Agreement No. 70NANB0H3038 awarded by the National Institute of Standards & Technology (NIST).

BACKGROUND OF THE INVENTION

1. Field of the Invention

The present invention generally relates to methods and systems for inspection of a specimen using different inspection parameters. Certain embodiments relate to computer-implemented methods for determining optimal parameters for inspection of a specimen based on defects selected for detection. Other embodiments relate to methods and systems for inspection of a specimen using different inspection modes.

2. Description of the Related Art

For many years, various brightfield, darkfield, and e-beam scanning methodologies have been used to inspect surfaces. These scanning technologies make use of radiation scattered, diffracted, and/or reflected by a surface to characterize and examine features of the surface. In particular, such scanning technologies are used to examine surfaces to determine the presence and location of defects in an inspected surface. The details of these and other related scanning and inspection technologies are well known to those having ordinary skill in the art.

Typically, such devices examine a surface by projecting a light beam onto the surface and then detecting resulting patterns of light received from the surface. Also typically, light beams are projected onto the surface over a single frequency (e.g., as typified by laser devices) or over a bandwidth of frequencies (such as can be obtained using appropriately filtered arc lamps).

In an effort to identify defects of ever decreasing sizes, conventional tools typically rely on illumination sources having shorter and shorter wavelengths. As is well-known to those having ordinary skill in the art, illumination of a surface with shorter wavelengths of light can be used to obtain greater resolution in images of the surface. Previously, greater resolution has been thought to be the key to improving defect detection of smaller defects. The inventor has discovered that greater resolution is only part of the defect identification story.

A common implementation of a conventional inspection tool is shown by the simplified schematic representation of a bright field inspection tool 100 shown in FIG. 1. An object 102 (commonly, a wafer) is secured to a movable stage 101 where it is illuminated by a light beam 103 produced by a single light source 104. Commonly, the light source 104 comprises a single arc lamp selectively filtered to produce a defined bandwidth of frequencies. In some alternatives, the light source 104 comprises a laser tuned to produce a single frequency coherent beam of light centered at some peak wavelength. Commonly, the light beam 103 is directed onto a partially transmissive surface 105 that reflects a portion of the light beam 103 through an objective lens system 106 which directs the beam 103 on the surface 102. Typically, different portions of the object 102 are successively inspected by scanning the substrate. Commonly, the stage mounted object 102 is scanned by moving the stage 101 as directed by a scanning control element 110. As the surface 102 is scanned, light reflected, scattered, diffracted, or otherwise received from the surface 102 passes through the objective 106 and passes back through the partially transmissive surface 105 into an optical system 107 that optimizes the light for detection with a detector system 108. Commonly, such optimization includes magnification, focusing, as well as other optical processing. The detector 108 receives the light and generates an associated electrical signal which is received by image processing circuitry 109. The processing circuitry conducts defect analysis to locate defects in the object 102.

Conventional approaches to detecting defects and process variations in layers of a semiconductor substrate have operated under the assumption that greater resolution in an inspection tool translates into greater sensitivity to the presence of defects. The resolving power of optical inspection tools can be characterized by the "point-spread-function" (PSF) of the tool. The PSF is affected by a number of factors including, but not limited to, the optical quality of the lenses (or other optical elements) used in the focusing elements, the wavelength of light, numerical aperture (NA) of the objective lens system, pupil shape, as well as other factors. In general, the resolution of a system is related to the wavelength ($\lambda$) of the exposure source divided by the numerical aperture (NA) of the objective lens system. Therefore, shorter wavelengths can be used to produce greater resolution.

Thus, in the prior art the emphasis has generally been on generating inspection tools that use shorter wavelength illumination sources to obtain better resolution, and presumably better sensitivity to defects. Light sources operating at visible wavelengths and near ultraviolet wavelengths (e.g., from about 400 nm to about 300 nm) have long been used as illumination sources. For example, mercury (Hg) or mercury xenon (HgXe) arc lamps have been used as illumination sources in the near ultra-violet (UV) and visible ranges. But, in the continuing drive for greater resolution, shorter wavelength illumination is desirable. Because the power of Hg and HgXe sources drops off rather dramatically, below 300 nanometers (nm) they are not excellent sources of deep UV (e.g., wavelengths below about 300 nm) illumination. Deep UV (DUV) lasers are a commonly used illumination source in the DUV range. Due to the rather high cost of such sources (especially, the laser sources), no known inspection tools or methods have implemented two (or more) sources to inspect surfaces. In fact, until now there was no reason to attempt to do so. The conventional approach has generally been to devise the shortest wavelength system and implement such a system to obtain the best possible resolution.

Although existing inspection machines and processes accomplish their designed purposes reasonably well, they have some limitations. There is a need for greater sensitivity than is currently provided by existing machines and processes. For these and other reasons, improved surface inspection tools and methodologies are needed.

SUMMARY OF THE INVENTION

In accordance with the principles of the present invention, an apparatus and method for inspecting a surface are disclosed. In particular, the method and apparatus are capable of inspecting a surface in two (or more) optical regimes thereby enhancing the defect detection properties of such method and apparatus.

In one embodiment, the invention describes a method for inspecting a substrate surface. The method involves providing a substrate characterized by an opacity transition wavelength. A first optimal inspection wavelength band is determined. The first optimal inspection wavelength band is selected from the wavelengths in the opaque regime defined by wavelengths shorter than the opacity transition wavelength of the substrate. A second optimal inspection wavelength band is determined. The second optimal inspection wavelength band is selected from the wavelengths in the transmissive regime defined by wavelengths longer than the opacity transition wavelength of the substrate. The substrate is illuminated with selected wavelengths of light that include at least one of the first optimal inspection wavelength band, the second optimal inspection wavelength band, or both the first optimal inspection wavelength band and the second optimal inspection wavelength band. The resulting optical signals are detected and used to generate associated electronic signals that are processed to detect defects and process variations in the surface.

In another embodiment, the invention comprises a surface inspection method involving illuminating the surface in two optical regimes. The method involves illuminating the surface with light in at least one of a first wavelength range and a second wavelength range. The first wavelength range is selected so that the surface is opaque to the light of the first wavelength range. The second wavelength range is selected so that the surface is at least partially transmissive to light in the second wavelength range. The resultant optical signals are detected and used to generate an associated electronic signal that is processed to detect defects and process variations in the surface.

Another embodiment of the invention includes an apparatus for detecting defects in an inspected surface. The embodiment includes an illumination element capable of providing illumination in at least two light modes. The first mode of operation of the illumination element provides first wavelengths of light, selected for inspection of the surface in an optical regime where the surface is opaque to said first wavelengths of light. The light of the first mode produces a resultant optical signal that is predominated by diffractive and scattering properties of the surface. The illumination element also includes a second mode of operation that provides wavelengths of light in a second optical regime where the surface is at least partially transmissive to said second wavelengths of light, thereby producing a resultant optical signal that is predominated by thin film optical properties of the surface. The apparatus is configured to inspect the surface using light in the first mode or in the second mode or in both modes simultaneously. The apparatus further includes a scanning element that enables the apparatus to scan the desired portions of the inspected surface and an optical system for receiving the resultant optical signal from the inspected surface and for producing an associated electronic signal. The apparatus also includes electronic circuitry for processing the electronic signal. Such processing can be used for identifying defects and process variations in the surface.

A different embodiment relates to a computer-implemented method that includes determining optimal parameters for inspection of a specimen based on defects selected for detection on the specimen. In one embodiment, the defects may be selected by a user. According to another embodiment, the defects may include relatively low contrast defects. The specimen may be a wafer or a reticle. Determining the optimal parameters may include performing one or more test inspections of the specimen with different parameters and identifying which of the different parameters produces the largest capture rate of the defects. In another embodiment, determining the optimal parameters may include performing one or more test inspections of a test specimen, known to have one or more of the defects, with different parameters and identifying which of the different parameters produces the largest capture rate of the defects. In some embodiments, determining the optimal parameters may include determining which of the different parameters produces the largest capture rate of the defects without increasing the number of false defects that are detected. In one embodiment, identifying which of the different parameters produces the largest capture rate may include classifying defects detected during the one or more test inspections. In a different embodiment, identifying which of the different parameters produces the largest capture rate may include automatically classifying defects detected during the one or more test inspections.

The method also includes setting parameters of an inspection system at the optimal parameters prior to the inspection of the specimen. In one embodiment, the optimal parameters may result in more of the defects being detected during the inspection than that which would be detected during the inspection using other parameters. In another embodiment, the optimal parameters may result in fewer non-selected defects being detected during the inspection than that which would be detected during the inspection using other parameters. In an additional embodiment, the optimal parameters may result in the number of false defects detected during the inspection that is equal to or less than that which would be detected during the inspection using other parameters. Setting the parameters may be performed by a computer. The method may include any other step(s) described herein.

An additional embodiment relates to a method for inspecting a specimen. In one embodiment, at least a portion of a surface of the specimen may include polysilicon, single crystal silicon, silicon dioxide, silicon nitride, or any combination thereof. The method includes illuminating the specimen with light having at least one wavelength below about 350 nm using a first subsystem and with light having at least one wavelength above about 350 nm using a second subsystem. In some embodiments, illuminating the specimen may include illuminating the specimen using the first and second subsystems substantially simultaneously. In other embodiments, illuminating the specimen may include illuminating the specimen using the first and second subsystems at different times. The first and second subsystems may be optimized for each of the at least one wavelength below and above about 350 nm, respectively.

In one embodiment, the first subsystem may include a laser. In another embodiment, the second subsystem may include a laser. In some embodiments, the first and second subsystems may include a common laser. In a different embodiment, the first subsystem may include a first laser, and the second subsystem may include a second laser. In other embodiments, the second subsystem may include a polychromatic light source. For example, the second subsystem may include an arc lamp. In some embodiments, the first and second subsystems may include a common polychromatic light source. In other embodiments, the first subsystem may include a first polychromatic light source, and the second subsystem may include a second polychromatic light source.

The method also includes collecting light from the specimen. In one embodiment, the collected light may include a bright field image of at least a portion of the specimen. In addition, the method includes detecting the collected light to produce signals representative of the collected light. In one embodiment, the at least one wavelength of the second subsystem is selected to increase contrast in the signals for a material of the specimen. In addition, at least the one wavelength of the first subsystem may be selected to increase sensitivity to the defects. The method further includes processing the signals to detect defects or process variations on the specimen. In one embodiment, the first subsystem may include a dark field illumination source. In one such embodiment, processing the signals may include Fourier filtering the signals corresponding to the collected light resulting from illuminating the specimen using the first subsystem. This method may also include any other step(s) described herein.

A further embodiment relates to a different method for inspecting a specimen. The method includes illuminating the specimen. In one embodiment, illuminating the specimen may include illuminating the specimen with light having at least one wavelength below about 350 nm and illuminating the specimen with light having at least one wavelength above about 350 nm. The method also includes collecting light from the specimen. In addition, the method includes detecting the collected light to produce optical phase signals representative of a first portion of the collected light and brightfield optical signals representative of a second portion of the collected light. The method further includes processing the optical phase signals and the brightfield optical signals separately to detect defects or process variations on the specimen. The method may also include any other step(s) described herein.

Another embodiment relates to a system configured to inspect a specimen. The system includes a first optical subsystem coupled to a broadband light source. The broadband light source may be configured to generate visible light, ultraviolet light, deep ultraviolet light, or a combination thereof. In one embodiment, the first optical subsystem may include an ellipsoidal mirror configured to produce a substantially aberration-free image of the broadband light source. In a different embodiment, the first optical subsystem may include an ellipsoidal mirror configured to provide substantially efficient coupling of light from the broadband light source to a third optical subsystem.

In some embodiments, the first optical subsystem may also include a beam shaping element configured to direct edge radiance of the broadband light source to a central portion of a pupil of the first optical subsystem for brightfield illumination. In another embodiment, the first optical subsystem may include a beam shaping element configured to alter a beam profile of the broadband light source such that the beam profile is substantially uniform. In an additional embodiment, the first optical subsystem may include a double zooming element configured to alter an optical invariant of the broadband light source. In some embodiments, the first optical subsystem may include a light pipe, which may be disposed between individual zooming elements of the double zooming element.

The system also includes a second optical subsystem coupled to a laser. In one embodiment, the laser may be configured to generate light having a wavelength less than about 350 nm. In a different embodiment, the laser may be configured to generate light having a wavelength less than about 266 nm.

The system further includes a third optical subsystem configured to couple light from the first and second optical subsystems to an objective. In some embodiments, the third optical subsystem may also be configured to allow substantially efficient coupling of the light from the second optical subsystem to the objective. The objective is configured to focus the light onto the specimen. In one embodiment, the objective may also be configured to illuminate the specimen with light from the first and second optical subsystems substantially simultaneously. In some embodiments, the third optical subsystem may include a polarization beamsplitter, which is configured to direct the light from the second optical subsystem to a dichroic beamsplitter. The dichroic beamsplitter may be configured to direct the light from the second optical subsystem to the objective. In one embodiment, the dichroic beamsplitter may also be configured to direct at least a portion of the light from the first optical subsystem to the objective.

In addition, the system includes a detection subsystem configured to detect light from the specimen and to produce signals representative of the detected light. In some embodiments, the light from the specimen may pass through the objective to the dichroic beamsplitter, which may direct the light from the specimen to the polarization beamsplitter. The polarization beamsplitter may also be configured to direct the light from the specimen to the detection subsystem. Furthermore, the system may include a processor configured to process the signals to detect defects or process variations on the specimen. The system may be further configured as described herein.

An additional embodiment is related to a different system configured to inspect a specimen. The system may include a first illumination subsystem, which is configured to illuminate the specimen with light having a wavelength less than about 350 nm. The system may also include a second illumination subsystem configured to illuminate the specimen with light having a wavelength greater than about 350 nm. The first and second illumination subsystems may have different illumination apertures. In one embodiment, the first and second illumination subsystems may be configured to illuminate the specimen in a narrow-band mode. In a different embodiment, the first illumination subsystem may be configured to illuminate the specimen in a narrow-band mode while the second illumination subsystem may be configured to illuminate the specimen in a broadband mode. In some embodiments, the first and second illumination subsystems may be configured to illuminate the specimen substantially simultaneously.

The system further includes a first detection subsystem configured to detect a first portion of light from the specimen. In addition, the system includes a second detection subsystem configured to detect a second portion of light from the specimen. The first portion of light and the second portion of light may have at least one different characteristic. The different characteristics may include, for example, different wavelengths and/or different polarizations. In some embodiments, the first and second detection subsystems may have different magnification settings. For example, the first portion of light, which is detected by the first detection subsystem, may be produced by illuminating the specimen using the first illumination subsystem. In such an embodiment, the first detection subsystem may have a magnification setting that is higher than a magnification setting of the second detection subsystem. In one embodiment, the first and second detection subsystems may be configured to detect the first and second portions of light substantially simultaneously.

Furthermore, the system may include a processor configured to process signals produced by the first and second detection subsystems to detect defects or process variations on the specimen. In some embodiments, the system may also include an auto-focus subsystem configured to operate at wavelengths within about 80 nm of the wavelength greater than about 350 nm. The system may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIGS. 15(a), 15(b), 16(a), and 16(b) are schematic diagrams illustrating various embodiments of combinations of multiple detection subsystems that may be incorporated into an inspection system;

FIG. 17 is a schematic diagram illustrating field coverage of a specimen and the corresponding TDI images; and FIG. 18 is a schematic diagram illustrating one path arrangement for a detection subsystem configured such that images of a specimen can be directed to any portion of a TDI.

Figure 1:
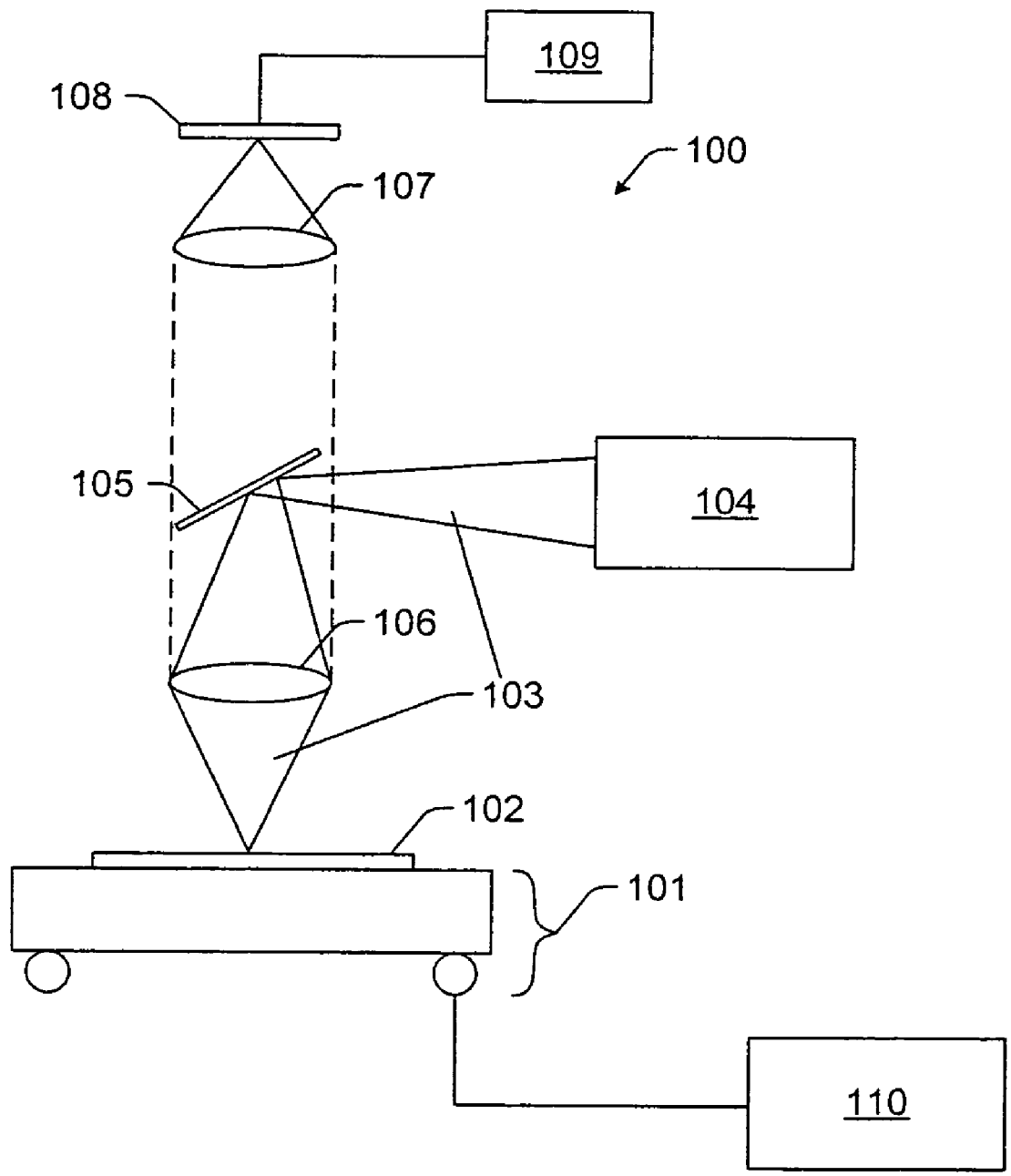
FIG. 1 depicts a conventional bright field surface inspection tool of a type known in the art.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The inventor has discovered that increasing resolution in an inspection tool does not necessarily correlate to increased sensitivity to defects. In fact, illuminated substrates demonstrate a number of heretofore unappreciated optical properties which can be advantageously exploited by embodiments of the invention in order to achieve high signal-to-noise ratios and increased sensitivity to defects. The inventor has discovered that illuminating an object with more than one frequency of light can actually yield better defect detection results than simply employing the highest resolution system. Semiconductor substrates, being constructed of many layers of different materials, demonstrate a complex array of optical properties which have made the detection of defects in the substrates a difficult process.

However, the inventor has discovered methods of exploiting these differing material properties to increase the sensitivity of defect detection. As used herein, the term "surface" is intended to encompass the upper portions of a substrate including the several uppermost layers and related structures formed thereon as well as the surface itself. Such surfaces are composed of many layers of material (e.g., Si, SiGe, $SiO_2$, polysilicon, Ti, TiN, Ta, TaN, SiN, low-K dielectric materials, and many, many, other materials). Semiconductor surfaces demonstrate a number of optical properties that can enhance an inspection tool's ability to detect defects. Among the optical properties exhibited by substrate surfaces are the propensity of the surface to scatter light, the propensity of the surface to diffract light, and thin film optical properties exhibited by the surface. Moreover, all of these effects have wavelength dependent properties associated with them. Thus, as is the case with semiconductor substrates (and phase-shift masks) when a number of materials are used in many layers of varying thickness dimensions, their combined effects are complex and difficult to predict. However, the inventor has found a way to exploit these varied optical characteristics to enhance defect detection in a substrate surface. This will be discussed in greater detail herein below.

Figure 2:
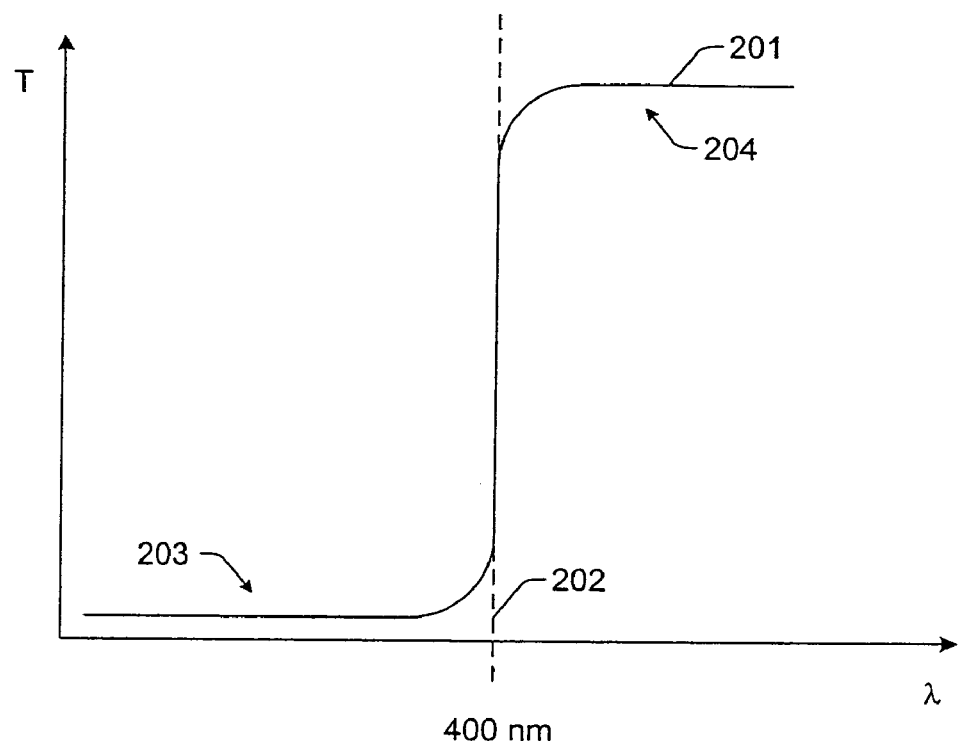
FIG. 2 is a simplified graphical representation of a transmission spectrum for a substrate including a depiction of an opacity transition wavelength for the substrate.

Many materials are used in the construction of semiconductor substrates. Particularly common materials include polysilicon and $SiO_2$. FIG. 2 graphically depicts the transmission spectrum 201 of a thin layer of polysilicon plotted as a function of wavelength (λ). A characteristic property of polysilicon is the opacity transition wavelength 202 around 400 nm (nanometers). As polysilicon is illuminated with relatively long wavelengths of light (i.e., wavelengths above transition wavelength 202), it behaves as a relatively transmissive material. However, when exposed to shorter wavelengths of light (i.e., wavelengths below the transition wavelength 202), polysilicon changes from a relatively transmissive material.

(i.e., in region 204) to a relatively opaque material (i.e., in region 203 where relatively little or no light is transmitted).

Figure 3A:
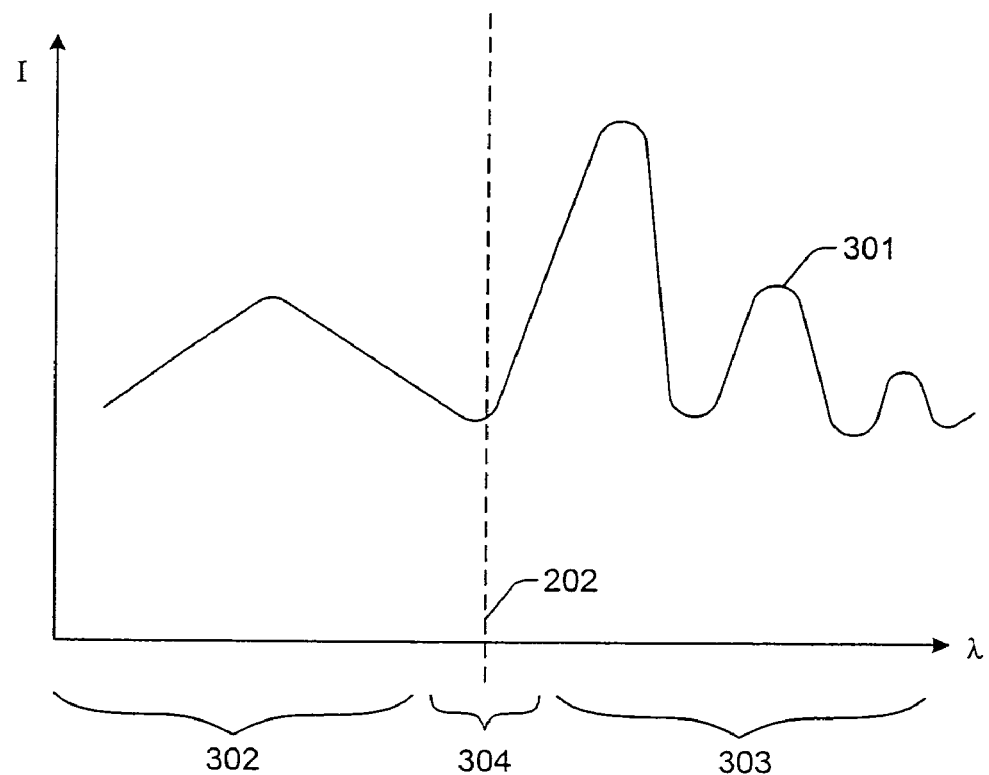
FIG. 3(a) is a simplified graphical depiction of a defect signal showing an opaque regime and a transmission regime.

An example of how such material properties can affect defect detection is illustrated with respect to FIG. 3(a). FIG. 3(a) is a graphical depiction of a "defect signal" produced by a defect associated with polysilicon structures (e.g., layers) on a typical semiconductor substrate. In the depicted figure, the defect signal intensity is plotted as a function of illumination wavelength. When a portion of a surface is illuminated, it produces a resultant optical signal (e.g., an image) that can be measured using a detector (e.g., a photodetector). A "defect signal" can be obtained by measuring the resultant optical signal for a portion of a surface containing a defect and comparing it to a resultant optical signal generated by a modeling program (or other suitable non-defect baseline) for the same portion of the surface. By subtracting out the defect-containing signal from the non-defect signal, a "defect signal" can be obtained.

The depicted example of FIG. 3(a) shows a defect signal 301 with signal intensity (I) plotted as a function of illumination wavelength ($\lambda$). The inventor has discovered that there appear to be two principle mechanisms for producing the defect signals. One mechanism is the diffraction and scattering from opaque surfaces. Another mechanism is the so-called thin film optical effects (e.g., thin film interference effects) caused by the transmissive and partially transmissive films and structures forming the surface. These mechanisms can be characterized as operating in two different optical regimes. The signal properties of these two different regimes are dramatically different and can be advantageously exploited to improve the sensitivity of inspection tools. In FIG. 3(a), a first regime 302 (also referred to herein as an opaque regime) and a second regime 303 (also referred to herein as a transmissive regime) are depicted. The opaque regime 302 defines a range of wavelengths that are shorter than the opacity transition wavelength 202. Light received from a surface illuminated by wavelengths of light in the opaque regime 302 demonstrates the anticipated ordinary diffraction and scattering properties expected when an opaque material is illuminated. For example, in the opaque regime 302, as the illumination wavelength decreases system resolution tends to increase.

In contrast, when the illumination wavelength ($\lambda$) is increased past a certain point, the light transmission behavior of the substrate changes. For purposes of this patent, wavelengths of light in this regime are said to belong to the transmissive regime. The transmissive regime 303 defines a range of wavelengths that are longer than the opacity transition wavelength 202. Light received from a surface illuminated by wavelengths of light in the transmissive regime 303 exhibits thin film optical properties as the predominant signal producing mechanism. In particular, at such longer wavelengths, the defect signal becomes largely dominated by optical interference properties induced by thin film structures on the substrate. As stated, these interference properties become the predominant mechanism producing the defect signal. At the opacity transition wavelength 202 many materials (especially thin films of such materials) experience this change in light transmission behavior.

Figure 3B:
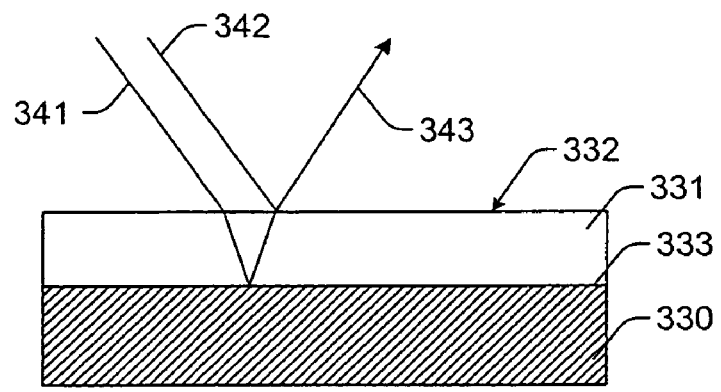
FIG. 3(b) is a simplified diagrammatic representation of a substrate used to illustrate aspects of thin film interference effects.

In order to obtain a more clear understanding of the previously described "transmissive" regime, reference is now made to FIG. 3(b). FIG. 3(b) schematically depicts a simplified example of a substrate surface. The surface includes a layer 330 of opaque material having another layer 331 formed thereon. At certain wavelengths the layer 331 is opaque. When such an opaque layer is illuminated with a light beam, the light is for the most part scattered and diffracted by the surface. Thus, such scattering and diffraction are the predominant mechanisms generating the resultant optical signal. However, for many materials, at certain wavelengths the layer 331 is at least partially transmissive. Under such conditions, thin film optical effects can be experienced by light beams directed onto the surface. One such effect is thin film interference. Thin film interference occurs when a light beam 341 passes through the partially (or wholly) transmissive material of layer 331 and combines into beam 343 with light beam 342 reflecting off the top surface 332 of layer 331. The resulting interference is a function of a number of factors. Such factors include, but are not limited to, the reflectivity of top surface 332, the reflectivity at the interface 333 between layer 330 and layer 331, absorption occurring in the layer 331 of partially reflective material, the wavelength of light used to illuminate the surface, and the optical thickness of the layer 331 of partially reflective material. Of course, all of these factors are influenced by the wavelength of the illuminating light. The interference can be either constructive or destructive depending upon the various factors. There can be many more layers involved, but the concept is the same. Another factor is the spread of wavelengths present. For example, lasers have no bandwidth and a long "coherence length," so interference can be produced in relatively thick layers. In broadband light beams, the coherence length can be fairly short, thereby causing interference in thinner layers. Coherence length is defined as $\lambda^2/\Delta\lambda$. The presence of a defect can alter the normal interference by changing the thickness or material properties of the surface, the defect itself, or its surroundings.

The opacity transition wavelength is different for each material. For example, polysilicon is very opaque to light at wavelengths below about 400 nm. However, at wavelengths above 400 nm polysilicon becomes a relatively transmissive material. The optical properties of a transmissive surface (or partially transmissive surface) are different than those of an opaque surface (where scattering and diffraction behavior predominate).

As briefly discussed herein above, when a substrate is illuminated by light having wavelengths in a transmissive regime 303, thin film optical properties predominate the signal producing mechanism. As noted above, such thin film optical properties include, but are not limited to, phase effects and interference effects caused by thin films. In the transmissive regime 303, the thin film optical properties result in a resultant optical signal that can resemble an oscillating waveform having peaks and valleys in light intensity that vary as the wavelength changes. Thus, in the transmissive regime 302, decreasing wavelength of the illumination source is not directly related to increased defect signal.

Returning to FIG. 3(a), the inventor has discovered that when inspecting for defects, almost all semiconductor materials demonstrate this "two-regime" wavelength dependent behavior. In practice, all that seems to differ from one material or defect to another is the wavelength of the transition region 304 (in particular, the opacity transition wavelength 202). Moreover, the inventor has discovered that this "two-regime" behavior can be exploited to achieve better defect capture rates than is possible for existing technologies.

The embodiments of the invention illuminate the substrate with a wavelength (or band of wavelengths) of light that is greater than the opacity transition wavelength and also with a wavelength (or band of wavelengths) of light that is shorter than the opacity transition wavelength. By doing so, a methodology using the combined signal can be used to achieve improved defect detection. Moreover, the principles of the invention are flexible. The illumination regimes need not be combined. The inspector can choose an inspection methodology that inspects using only a wavelength (or band of wavelengths) of light that is longer than the opacity transition wavelength alone. In an alternative methodology, the inspector can choose to inspect using only a wavelength (or band of wavelengths) of light that is shorter than the opacity transition wavelength alone. The inspector can then simply choose the inspection methodology that achieves the best defect capture ratios. Typically, the methodology obtaining the greatest signal-to-noise ratios (SNR) in the resultant optical signal is chosen as the desired inspection methodology. Using such methodologies, greater sensitivity in defect detection can be achieved. Furthermore, in accordance with the principles of the invention this sensitivity can be extended to detect defects in the sub-resolution range (i.e., defects of a smaller size than the resolving power of the system).

The inventor has discovered that the nature and properties of the opaque and transmission regimes and the wavelength of the opacity transition wavelength are determined by the surface characteristics (including material properties) of the layers of the substrate being inspected. As previously indicated, the resultant optical signal from the surface when illuminated is dominated by two general phenomena. First, when the surface layers are relatively opaque to the illuminating wavelengths of light, the optical signal is dominated by the light scattering and diffraction properties of the surface. Such opacity is a function of film thickness, the k (complex refractive index) of the film. As indicated, these properties are highly wavelength dependent. For example, polysilicon is very opaque at wavelengths below about 400 nm. In contrast, at wavelengths above 400 nm, polysilicon is a relatively transmissive material. Thus, the opacity transition wavelength for polysilicon is about 400 nm. As such, the opacity transition wavelength defines the transition region 204. Additionally, high-K dielectric materials (such as SiLK®, Black Diamond®, or FLARE®) generally have opacity transition regions in the range of 350-360 nm. Since the forgoing materials are particularly common in semiconductor fabrication, 350 nm is a particularly attractive wavelength for use in accordance with the principles of the invention. A more detailed discussion of this attractiveness is included in later paragraphs. Also, $SiO_2$ films have an opacity transition region at about 190 nm which makes this wavelength attractive.

As explained briefly hereinabove, the "transmissive" regime is an optical bandwidth of wavelengths wherein thin film properties of the substrate predominate as the cause of the resultant optical signal. Usually, a defect signal in a transmissive regime demonstrates a signal intensity curve having an oscillatory pattern of light intensity peaks and valleys that vary with the wavelength (See, for example, 303 of FIG. 3(a)). In general, this pattern is related to the constructive and destructive interference effects associated with thin film optical behavior. By way of contrast, the defect signal is dominated by diffraction and scattering effects of the substrate when illuminated with wavelengths of light chosen from the "opaque" regime. Such a defect signal is generally non-oscillatory (See, for example, 302 of FIG. 3(a)).

In general, embodiments of the invention are capable of illuminating the substrate in two different optical regimes (e.g., opaque and transmissive) and capable of detecting the resultant optical signal. Alternatively, a substrate can be illuminated by a light beam having wavelengths in the opaque regime alone. In another alternative, the substrate can be illuminated by a light beam having wavelengths in the transmissive regime alone. The resultant optical signals can be integrated, compared, or otherwise processed together to achieve defect detection. Usually, the approach that yields the best inspection results (e.g., the approach that provides the strongest signal, the best SNR, or some other suitably useful parameter) is employed for inspection.

A generalized method embodiment for inspecting a surface includes at least the following operations. Illuminating the surface with light in a first wavelength range selected such that the surface is opaque to the light of the first wavelength range. In such an opaque regime, a first resultant optical signal is produced that is predominated by diffractive and scattering properties of the surface. An example of such a regime is shown as 302 of FIG. 3(a). Also, the surface is illuminated with light in a second wavelength range selected such that the surface is at least partially transmissive to light in the second wavelength range. In such a transmissive regime, another resultant optical signal is produced that is predominated by thin film optical properties of the surface. An example of such a regime is shown as 303 of FIG. 3(a). The resultant optical signals are detected and processed to identify defects and unwanted process variations in the surface. As discussed, the substrate can also be illuminated by light having a wavelength in the opaque regime alone to obtain inspection information. Also as discussed, the substrate can also be illuminated by light having a wavelength in the transmissive regime alone to obtain inspection information.

The above steps can be supplemented with a step of determining an appropriate opacity transition wavelength (and thereby determine appropriate opaque and transmissive regimes) for the substrate. The opaque and transmissive regimes can be identified using a number of approaches. First, a substrate can be scanned at a number of wavelengths and a transition region for the substrate can be identified. Alternatively, transmission calculations using the k values of the substrate materials as a function of wavelength can be used to provide an optical picture of the wavelength dependent characteristics of a substrate (in particular, to determine the opacity transition wavelength or region). Once a transition region is identified, the substrate can be illuminated at a wavelength (or wavelengths) above the transition region and at a wavelength (or wavelengths) below the transition region so that signal generated by thin film optical properties and by the diffraction/scattering properties can be captured. Alternatively, the substrate can be illuminated at a wavelength (or wavelengths) above the transition region or at a wavelength (or wavelengths) below the transition region, which ever produces the best defect detection results.

Figure 4A:
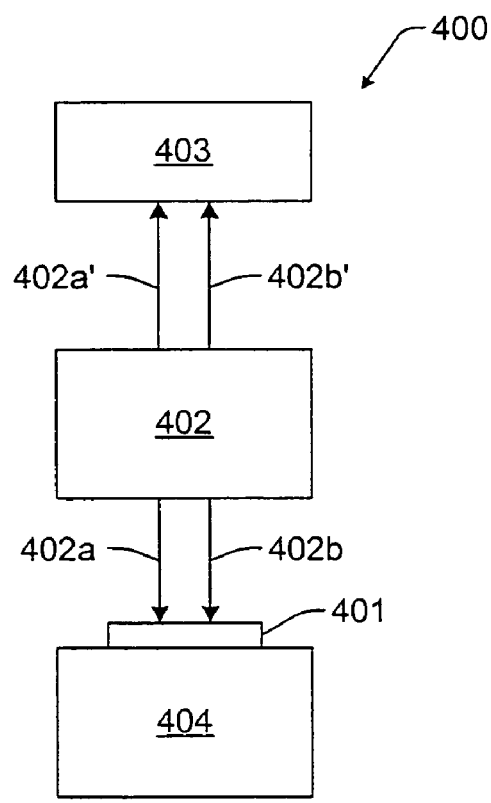
FIG. 4(a) is a simplified block depiction of a generalized inspection tool embodiment constructed in accordance with the principles of the invention.

FIG. 4(a) is a schematic block diagram illustrating an inspection tool 400 constructed in accordance with the principles of the invention. Such tools can include, without limitation, bright field type inspection tools, darkfield inspection tools, and combination bright field/darkfield inspection tools. The inventor notes that a bright field implementation is the preferred implementation. Such an apparatus includes an illumination element 402 for illuminating substrate 401. The illumination element 402 is configured so that it can illuminate the substrate 401 in two (or more) optical wavelength regimes. Typically, this is achieved by an illumination element 402 having two (or more) operative modes. A first mode is capable of illuminating the substrate 401 at a first set of wavelengths of light 402a selected for inspection of the surface in a first optical regime where the surface is opaque to the first set of wavelengths of light 402a. This first mode produces a first resultant optical signal 402a' that is predominated by diffraction and scattering of light from the substrate. Additionally, the illumination element 402 is capable of operating in a second mode that illuminates the substrate 401 at a second set of wavelengths of light 402b selected for inspection of the substrate surface in a second optical regime where the surface is at least partially transmissive to the second set of wavelengths of light 402b. This second mode produces a second resultant optical signal 402b' that is predominated by the thin film optical properties of the substrate 401. Typically, the first mode illuminates the substrate with light at wavelengths selected so that they are below an opacity transmission wavelength for the inspected substrate. Also, the second mode illuminates the substrate with light at wavelengths selected such that they are above the opacity transmission wavelength for the inspected substrate. Thus, in one preferred implementation, a first mode illuminates a substrate using wavelengths of less than about 350 nm and illuminates in a second mode with wavelengths above about 350 nm. In another preferred implementation, a first mode illuminates a substrate using wavelengths of less than about 400 nm and illuminates in a second mode with wavelengths above about 400 nm. In still another preferred implementation, a first mode illuminates a substrate using wavelengths of less than about 190 nm and illuminates in a second mode with wavelengths above about 190 nm.

The first resultant optical signal 402a' and the second resultant optical signal 402b' are received by detector system 403. The detector system 403 processes the received resultant optical signals (402a', 402b') to identify defects and/or process variations in the inspected surface. Typically, the system also includes a scanning element 404 that enables the apparatus to scan the desired portions substrate. Such scanning can be achieved by a number of means known to persons having ordinary skill in the art. For example, the illuminating light can be moved over the desired portions of the surface until the substrate is scanned. Alternatively, the substrate can be moved so that the light is scanned over the desired portions of the surface thereby scanning the substrate.

In one implementation, an inspection tool 400 such as depicted in FIG. 4(a) can be operated as follows. A substrate 401 having a number of known defects is positioned in the tool. Each defect is illuminated at a variety of wavelengths to determine the optimal wavelength (or combination of wavelengths) for producing the best defect capture rate for each defect. Then, the substrate is inspected at the optimal wavelength (or combination of wavelengths). In one implementation, this can be accomplished as follows.

A number of defects (of known types and sizes) on substrate 401 are illuminated using a first series of different wavelengths selected from the first set of wavelengths of light 402a in the opaque regime. For example, if the opacity transition wavelength for the substrate is determined to be 350 nm, the first series of different wavelengths (i.e., those in the opacity regime) is selected from wavelengths shorter than 350 nm. Defects can be illuminated, for example, at wavelengths of 340 nm, 330 nm, 320 nm, 310 nm, and so on. Any series of wavelengths in the opaque regime (here, wavelengths of less than 350 nm) can be chosen. The first resultant optical signals 402a' are then detected and compared to determine the optimal inspection wavelength(s) in the opaque regime. For example, wavelength(s) producing the best SNR can be used as the optimal wavelength(s).

Similarly, the defects are also illuminated using a second series of different wavelengths selected from the second set of wavelengths of light 402b in the transmissive regime. Continuing the example, for a substrate having an opacity transition wavelength of 350 nm, a second series of different wavelengths (i.e., those in the transmission regime) are selected from wavelengths longer than 350 nm. For example, the defects can be illuminated at wavelengths of 360 nm, 370 nm, 380 nm, 390 nm, and so on. Any series of wavelengths in the transmission regime (here, wavelengths of longer than 350 nm) can be chosen. The second resultant optical signals 402b' are then detected and compared to determine the optimal inspection wavelength(s) in the transmissive regime. For example, wavelength(s) producing the best SNR can be used as the optimal wavelength(s).

Figure 4B:
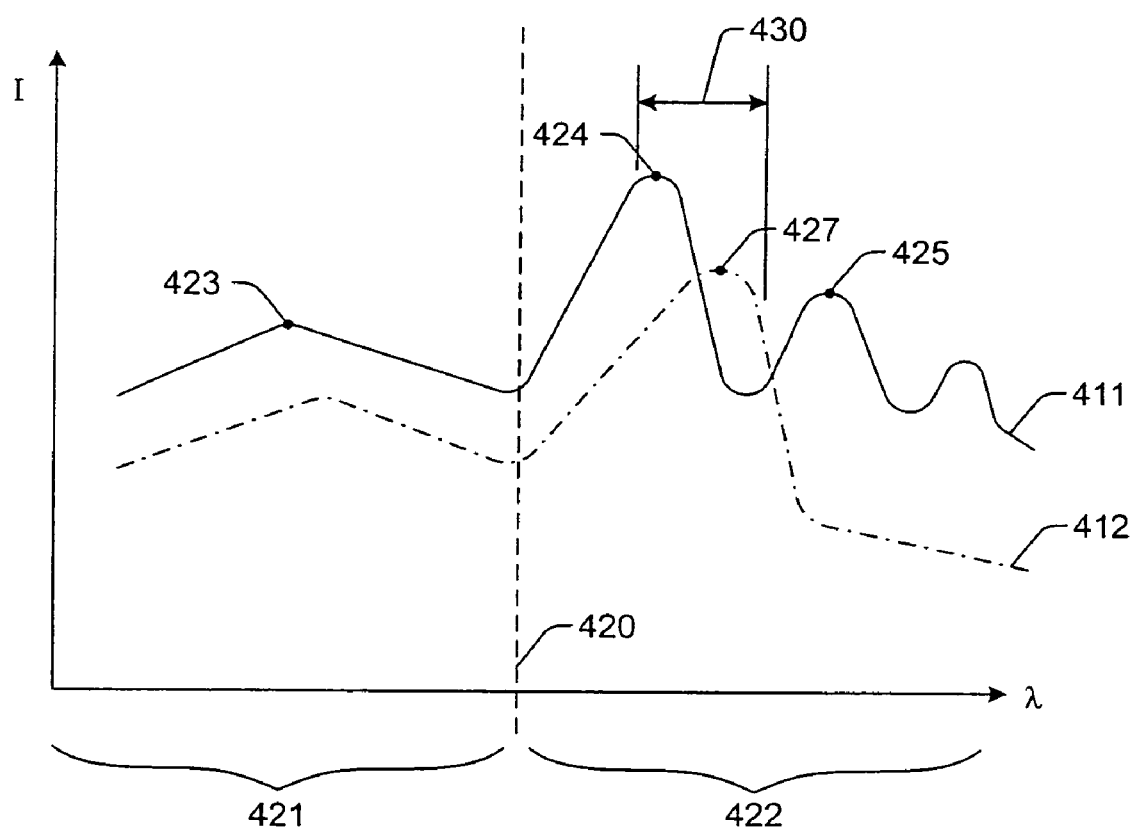
FIG. 4(b) is a simplified graphical depiction of a pair of defect signals showing an opaque regime and a transmission regime and also illustrating optimal wavelengths (or wavelength bands) for inspection in each regime.

An example of how this works can be illustrated with respect to FIG. 4(b) which graphically depicts a pair of defect signals located on a substrate 401. One defect signal 411 is for a first defect and another defect signal 412 is for a second defect. An opacity transition wavelength 420 for the relevant portions of the substrate is also depicted. Also shown are an associated opaque regime 421 and an associated transmissive regime 422.

By illuminating the surface with a series of wavelengths in the opaque regime 421, optimal wavelength(s) for detecting a defect signal in the opaque regime can be then determined. For example, for the first defect this wavelength corresponds to point 423 (on the defect signal 411) where the signal caused by scattering and diffraction has the maximum SNR (and most likely the highest defect capture ratio). It should be pointed out that the optimal wavelength can correspond to a band of wavelengths.

Similarly, the defects are also illuminated using the second series of different wavelengths in the transmissive regime. The second resultant optical signals 402b' are detected and compared to determine the optimal wavelength(s) producing the best defect capture ratio in the transmissive regime. Again referring to FIG. 4(b), the defect signal 411 can have a signal maxima at several different wavelengths (e.g., at points 424, 425). Thus, the amplitude of the defect signal produced by each wavelength is compared to determine the optimal wavelength in the transmissive regime 422. For example, the wavelength corresponding to point 424 of the defect signal 411 appears to offer the best SNR.

Additionally, the optimal wavelengths may be modified to capture more than one type of defect. For example, another type of defect (indicated by defect signal 412) may have a differently shaped signal curve. In the transmissive regime 422, the defect signal 412 has a signal maxima at a wavelength corresponding to point 427. The process for finding the optimal inspection wavelengths proceeds as explained herein above. During such a process, it will be determined that the defect signal 412 has a signal maxima at a wavelength corresponding to point 427. In order to achieve the best capture ratio for both types of defects, a band of wavelengths in the transmissive regime may provide superior defect identification. For example, a waveband 430 that encompasses the optimal wavelengths (corresponding to points 424, 427) for both types of defects can be used to maximize defect capture for both types of defects. Additionally, in some implementations, the best signal is received if the defects are illuminated with wavelengths in both regimes to obtain a composite defect signal. Thus, defects can be illuminated with wavelengths of light in the opaque regime or the transmissive regime or in both regimes depending on which approach yields the best defect capture rate.

Figure 5:
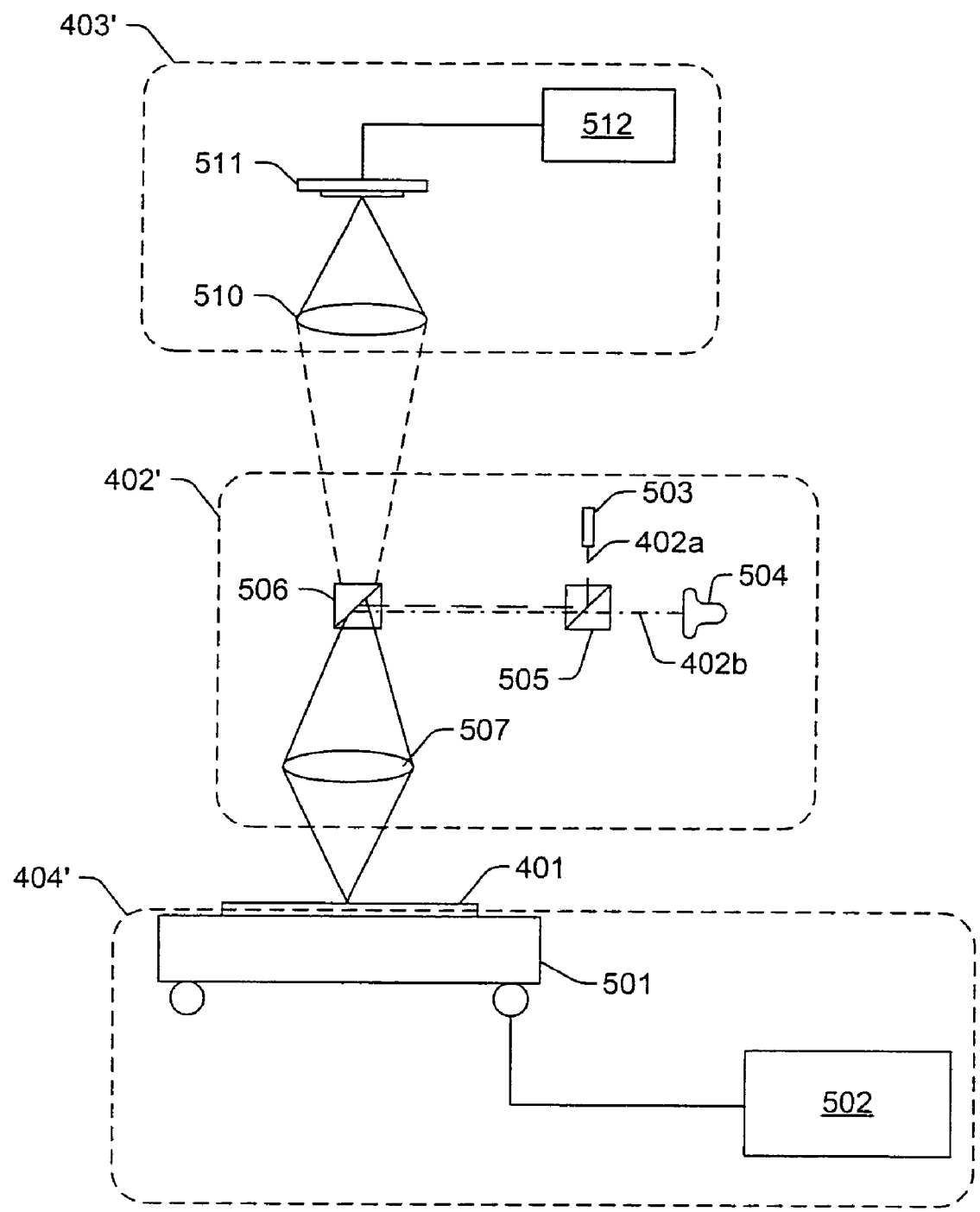
FIG. 5 is a simplified schematic depiction of an embodiment of an inspection tool constructed in accordance with the principles of the invention.

FIG. 5 is a simplified schematic depiction of one type of bright field inspection tool embodiment constructed in accordance with the principles of the invention. A substrate 401 is positioned in the tool so that it can be inspected. In the depicted embodiment, the substrate 401 is mounted on a movable stage 501 in readiness for inspection. The scanning of the stage 501 can be controlled with electronic circuitry comprising a scanning control element 502. The movable stage 501 and its control element 502 can all be included as part of a scanning element 404'. It is to be noted that the substrate 401 can be arranged on a movable stage 501 or any other type of support structure commonly used in such inspection tools. In alternative embodiments, the scanning control element 502 can be used to move other elements of the inspection tool in order to effectuate scanning of the desired portions of the substrate 401 being inspected.

With continued reference to FIG. 5, a pair of illumination sources 503 and 504 are used to generate the two operative modes of the illumination element 402'. The first illumination source 503 illuminates the substrate 401 at wavelengths below the opacity transition region, and the second illumination source 504 illuminates the substrate 401 at wavelengths above the opacity transition region. As stated, the first illumination source 503 illuminates the substrate 401 at a first set of wavelengths of light (depicted by the dashed line 402a). As previously explained, the first set of wavelengths of light operates in a first optical regime where the surface is opaque to the first set of wavelengths of light 402a. An example of such a first illumination source 503 is a neodymium YAG laser tuned to produce an output beam of 266 nm. However, any laser capable of producing light having wavelengths of less than about 350 nm can be used. Alternatively, other lasers capable of producing light beams having wavelengths of less than about 400 nm can also be used. Also, as previously explained, a suitable first illumination source 503 is any light source capable of operating at wavelengths where the substrate produces a resultant optical signal that is predominated by diffractive and scattering properties of the substrate. Such sources include, without limitation, polychromatic sources (e.g., arc lamps) and lasers.

With continued reference to FIG. 5, a second illumination source 504 illuminates the substrate 401 at a second set of wavelengths of light (depicted by the dotted/dashed line 402b). As previously explained, the second set of wavelengths of light operates in a second optical regime above the opacity transition region (e.g. at wavelengths where the surface is at least partially transmissive to the light 402b). This second mode produces a second resultant optical signal 402b' that is predominated by the thin film optical properties of the substrate 401. An example of such a second illumination source 504 is a mercury xenon (HgXe) arc lamp which can produce a wide range of light in the visible and near UV spectrum. However, any light source capable of producing light having wavelengths of greater than about 350 nm can be used. Alternatively, in other embodiments, light sources (e.g., lasers) capable of producing light beams having wavelengths of greater than about 400 nm can also be used. Also, as previously explained, a suitable second illumination source 504 comprises any light source capable of operating at wavelengths where the substrate produces a resultant optical signal that is predominated by thin film optical properties of the substrate 401. Such sources include, without limitation, polychromatic sources (e.g., arc lamps) and lasers.

In the depicted embodiment, both the sources 503, 504 are directed onto a dichroic beam splitter 505. The dichroic beam splitter 505 is constructed such that (in this implementation) it is reflective to light having wavelengths below a certain wavelength and transmissive to wavelengths of light above a certain wavelength. In one example, the dichroic beam splitter 505 is transmissive to light having wavelengths above the opacity transition region of the substrate and reflective to light having wavelengths below the opacity transition region of the substrate. In the depicted example, the dichroic beam splitter 505 is reflective to wavelengths of light below 350 nm (e.g. 266 nm light produced by a laser source 503) and transmissive to wavelengths of light above 350 nm (e.g., a portion of the spectrum produced by an HgXe arc lamp source 504). Such dichroic beam splitters are well known to persons having ordinary skill in the art and available from many different manufacturers.

The light passes through the dichroic beam splitter 505 onto a second beam splitter 506 that directs a portion of the light downward toward the substrate 401 where it passes through an objective lens system 507. The objective lens system 507 corrects aberrations and focuses the light on the substrate 401 for inspection. The objective lens system 507 can comprise many different optical elements. The construction of such objective lens systems 507 are well known to those having ordinary skill in the art and therefore will not be described in detail here. Because lens systems capable of operating over large bandwidths of wavelengths are somewhat difficult to design and fabricate, separate optical components can be implemented for each waveband in order to obtain good optical image quality. For example, a separate narrow band objective lens and associated lenses can be used for operation with a laser operating at a wavelength of 266 nm. A second, wide band objective lens and associated lenses can be implemented for use above 360 nm where a Hg or HgXe lamp operates as the illumination source. For example, in such an implementation, an Hg lamp can be filtered to use only g-line (404nm) and/or i-line (436 nm) light in regions where polysilicon is optically transmissive.

Light directed onto the substrate 401 produces a resultant optical signal which passes back through the objective lens systems 507 and second beam splitter 506 and into a detector system 403'. As explained with respect to FIG. 4, the resultant optical signal includes a first and second resultant optical signal (402a', 402b' as shown in FIG. 4) which are received by detector system 403'. The depicted detector system 403' includes a focusing element 510 that receives the resultant optical signals and focuses the received resultant optical signals onto a detector element 511. The focusing element 510 typically includes many optical elements that can be used to adjust the magnification, focus, aberration correction, resolution, and other optical properties of the system in order to enhance the tool's inspection characteristics. The construction of such focusing elements is well known to persons having ordinary skill in the art.

After the resultant optical signals pass through the focusing element 510, it is received by a detector element 511. The detector element 511 can comprise a wide range of photosensitive detector devices. Such devices include, without limitation, TDI (time delay integration) devices, CCD (charge coupled devices), photodiodes, PMT (photo multiplier tubes), as well as a wide range of related devices. The inventor also particularly contemplates that the depicted detector element 511 includes array type photosensitive detector devices. In one implementation, a preferred detector element 511 comprises a backside thinned TDI sensor array. Such arrays are available from many different manufacturers (e.g., from Hamamatsu Photonic KK of Hamamatsu Japan). Such a detector element 511 receives the resultant optical signals and transmits the signals as either electronic or optical information to image processing circuitry 512 for analysis. The image processing circuitry uses various image processing techniques and algorithms to analyze the resultant optical signal to identify defects. Such image processing circuitry 512 can include microprocessors, PLD's, ASIC's, DSP's, as well as a wide range of other digital or analog electronic devices known to persons having ordinary skill in the art.

Figure 6:
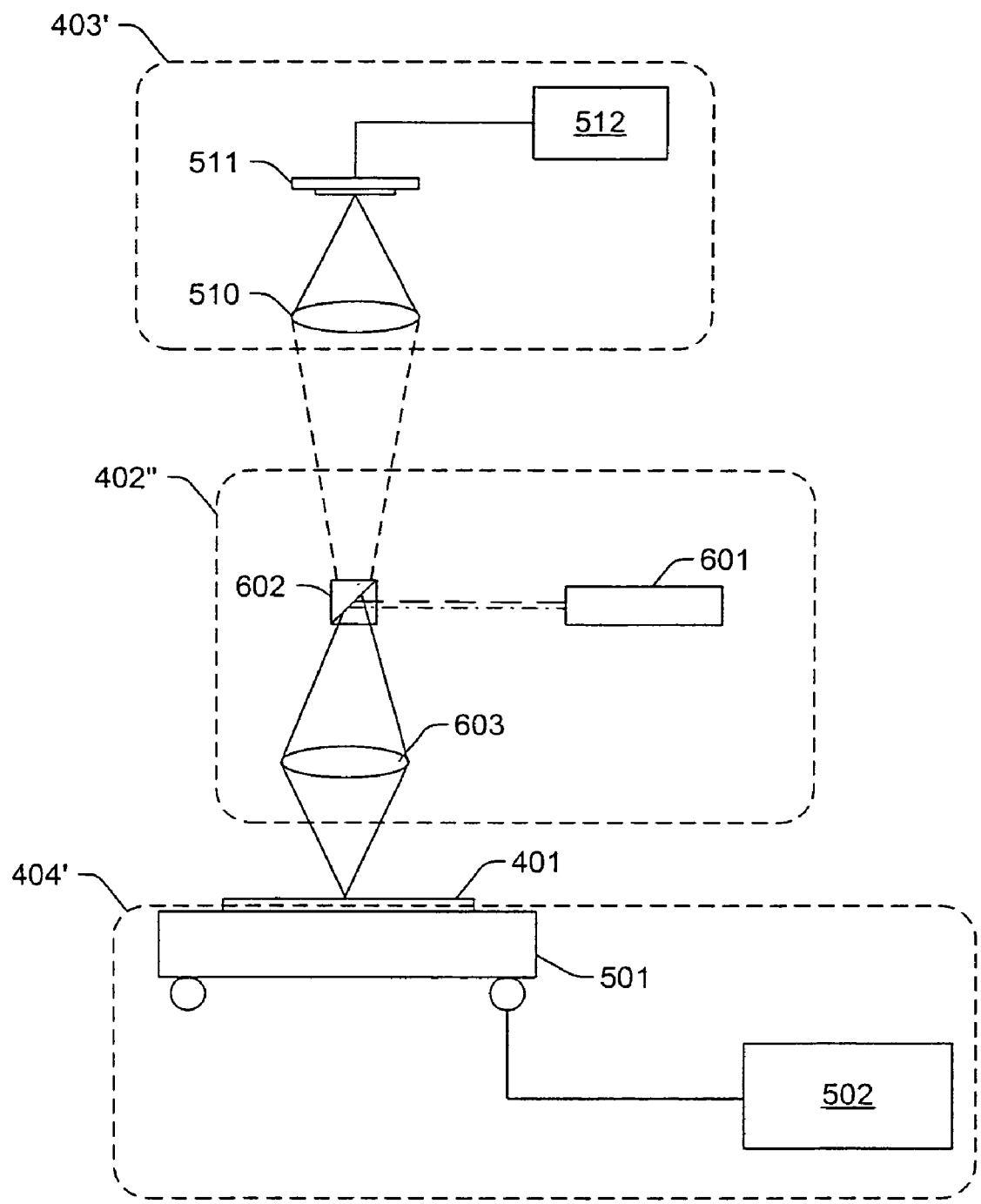
FIG. 6 is a simplified schematic depiction of another embodiment of an inspection tool constructed in accordance with the principles of the invention.

Another implementation is depicted in FIG. 6. The depicted embodiment is somewhat similar to the embodiment shown in FIG. 5. As with the embodiment of FIG. 5, the substrate 401 is positioned in the tool so that it can be inspected. As with the embodiment of FIG. 5, the substrate 401 is mounted on a movable stage 501 so that scanning can be controlled with electronic circuitry 502. The movable stage 501 and its controlling electronic circuitry 502 can all be included as part of a scanning element 404'.

One significant difference in the depicted embodiment is the configuration of the illumination element 402''. Instead of the pair of illumination sources 503 and 504 used in FIG. 5, a single illumination device 601 is used. In the depicted embodiment, a single illumination device 601 is used to generate the two operative modes of the illumination element 402''. Typically (but not exclusively), the illumination device 601 is a multi-wavelength laser device. In a first mode, the device 601 illuminates the substrate 401 at wavelengths below the opacity transition region and in a second mode illuminates the substrate 401 at wavelengths above the opacity transition region. As stated previously herein, the first mode illuminates the substrate 401 at a first set of wavelengths of light (depicted by the dashed line) that operates in a first optical regime where the surface is opaque to the first set of wavelengths of light. In the second mode of operation the illumination device 601 illuminates the substrate 401 at a second set of wavelengths of light (depicted by the dotted/dashed line) in a second optical regime where the thin film optical properties of the substrate predominate.

An example of such an illumination device 601 is a neodymium YAG laser. In the first mode, the laser can be tuned to produce an output beam of 266 nm (i.e., the $4^{th}$ harmonic of the laser). Additionally, the illumination device 601 can be tuned to produce an output beam of 532 nm (i.e., the $2^{nd}$ harmonic of the laser). Thus, the illumination device 601 can be tuned to illuminate the substrate 401 at a first set of wavelengths of light (depicted by the dashed line) and at a second set of wavelengths of light (depicted by the dotted/dashed line). As previously explained, the first set of wavelengths of light operate in a first optical regime (e.g. at wavelengths where the surface is relatively opaque to the light), and the second set of wavelengths of light operate in a second optical regime (e.g. at wavelengths where the surface is at least partially transmissive to the light). As previously explained, the first mode produces a first resultant optical signal that is predominated by the diffraction and scattering optical properties of the substrate 401, and the second mode produces a second resultant optical signal that is predominated by the thin film optical properties of the substrate 401. If a neodymium YAG laser is implemented as the illumination device 601, it can be tuned to produce an output beam at both 266 nm and 532 nm simultaneously. Thus, such an illumination device 601 can be used to produce wavelengths of light both above and below 350 nm to satisfy both modes of operation. Alternatively, for some other substrates, the illumination device 601 can be used to produce wavelengths of light both above and below 400 nm to satisfy both modes of operation. Using yet other devices 601, other opacity transition region wavelengths can be accommodated. Additionally, some types of polychromatic sources can be used (with appropriate filters) to accommodate such single source dual-mode operation.

The light produced in both modes is directed onto a beam splitter 602 which directs the light through an objective lens system 603 onto a desired portion of the substrate 401. The beam splitter 602 and objective lens system 603 are essentially the same systems as discussed hereinabove with respect to FIG. 5 and so will not be described in detail here.

Light directed onto the substrate 401 produces resultant optical signals which pass back through the objective lens systems 603 and beam splitter 602 and into a detector system 403'. As previously explained, the resultant optical signals are received by detector system 403' where they can be processed to detect defects or other surface charateristics. The depicted detector system 403' includes a focusing element 510 that receives the resultant optical signals and focuses the received resultant optical signals onto a detector element 511. Such a focusing element 510 and detector element 511 are as described previously (e.g., with respect to FIG. 5) and, therefore, will not be discussed here. The detector element 511 receives the resultant optical signals and transmits the signals as either electronic or optical information to image processing circuitry 512 for analysis. As with the image processing circuitry of the embodiment shown in FIG. 5, the image processing circuitry 512 uses various image processing techniques and algorithms to analyze the resultant optical signal to identify defects.

Figure 7:
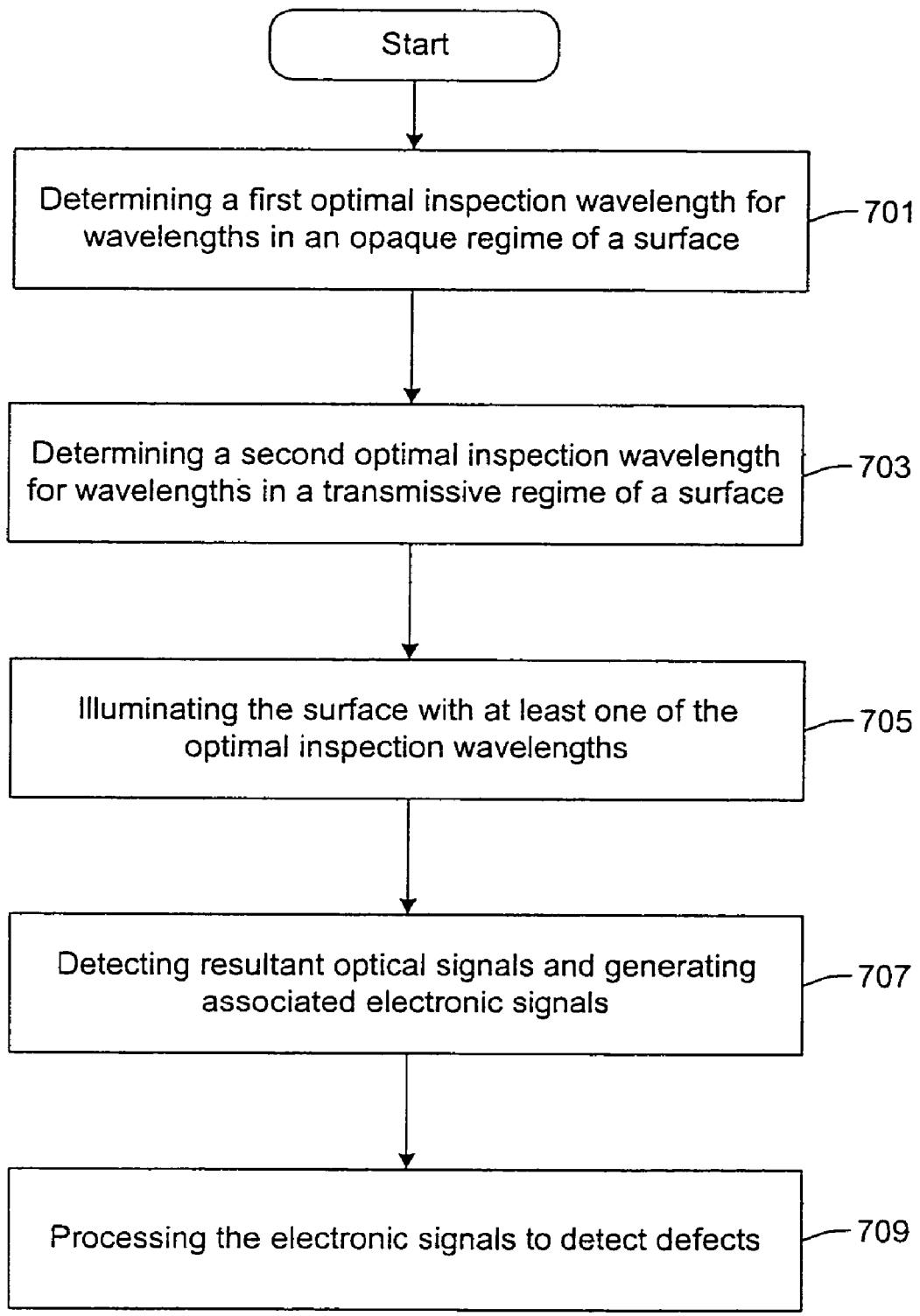
FIG. 7 is a flow diagram illustrating one embodiment of a process for inspecting a surface of a substrate in accordance with the principles of the present invention.

The above-described embodiments can implement methods for increasing the sensitivity and SNR of surface inspection techniques. FIG. 7 is a flow diagram illustrating one method of detecting defects in accordance with the principles of the invention.

The method includes determining a first optimal inspection wavelength (or waveband of many wavelengths) chosen from a first wavelength range selected such that the surface is opaque to the light of the first wavelength range (i.e., in the opaque regime), thereby producing a resultant optical signal that is predominated by diffractive and scattering properties of the surface (Step 701). As described hereinabove, this is typically achieved by illuminating a substrate defect(s) at several different wavelengths of light such that each of the wavelengths are shorter than the opacity transition wavelength for the substrate. The resultant optical signals are then compared to determine a first optimal wavelength (or wavelength band) that exhibits the best defect capture rate in the opaque regime. This determination can be based on a number of factors including, but not limited to, SNR and signal intensity.

The method includes determining a second optimal inspection wavelength (or waveband of many wavelengths) chosen from a second wavelength range selected such that the surface is at least partially transmissive to the light of the second wavelength range (i.e., in the transmissive regime), thereby producing a resultant optical signal that is predominated by thin film optical properties (e.g., thin film interference effects, etc.) of the surface (Step 703). As described hereinabove, this is typically achieved by illuminating a substrate defect(s) at several different wavelengths of light such that each of the wavelengths are longer than the opacity transition wavelength for the substrate. The resultant optical signals are then compared to determine a second optimal wavelength (or wavelength band) that exhibits the best defect capture rate in the transmissive regime. This determination can be based on a number of factors including, but not limited to, SNR and signal intensity.

Once optimal wavelengths (or bands of wavelengths) have been determined for the opaque and transmissive regimes, the surface is illuminated using selected wavelengths (or bands of wavelengths) (Step 705). It should be specifically noted that the illumination can be conducted in accordance with several schemes. The illumination can be conducted at the first optimal wavelength (or band of wavelengths) determined for wavelengths in the opaque regime. Alternatively, the illumination can be conducted at the second optimal wavelength (or band of wavelengths) determined for wavelengths in the transmissive regime. In still another approach, the illumination can be conducted at both the first optimal wavelength (or band of wavelengths) and the second optimal wavelength (or band of wavelengths) to obtain a combined defect signal generated by simultaneous illumination in both regimes. Although simultaneous illumination is preferred, sequential illumination schemes can also be used. Generally speaking, the selected illumination wavelength(s) are selected because they yield the best defect capture ratio. Generally, it is not known beforehand whether inspection in both regimes, or inspection in one regime or the other will yield the best defect capture ratio. In an optional step, a process of comparing the three indicated approaches can be conducted to find the best approach which can then be applied to a full inspection. Typically, the capture ratio is highest for resultant signals having the highest SNR.

Once illuminated, the resultant optical signals which result from said illumination of the substrate are detected and used to generate associated electronic signals (Step 707). The electronic signals are then processed to detect defects and process variations in the substrate (Step 709). A number of signal processing methods known to persons having ordinary skill in the art can be implemented with the present methodologies to obtain defect detection in accordance with the principles of the invention. Inspection in accordance with the principles of the invention can be performed after each process step in a semiconductor fabrication process.

Figure 8:
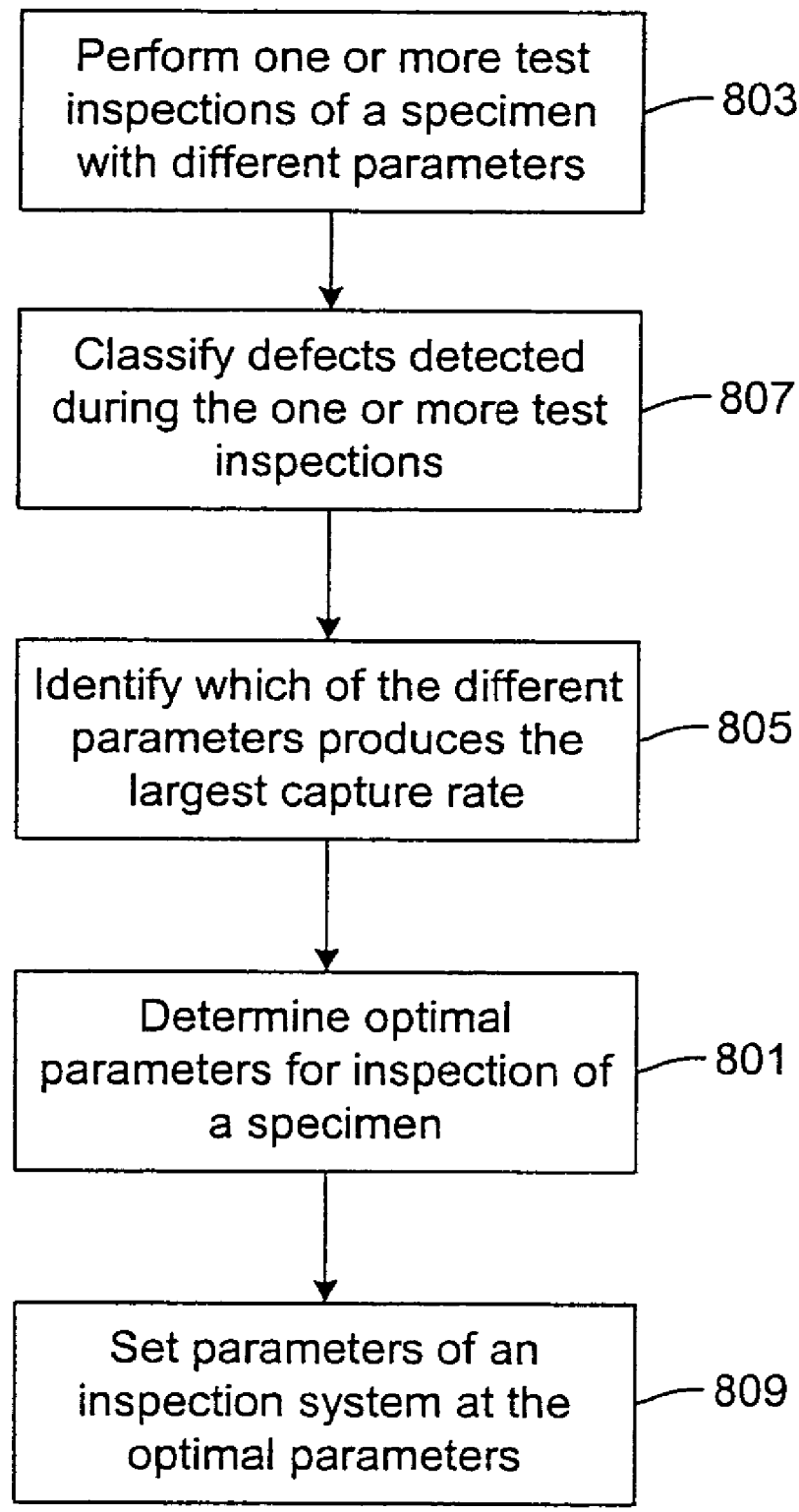
FIG. 8 is a flow diagram illustrating one embodiment of a computer-implemented method for determining optimal parameters for inspection of a specimen.

FIG. 8 illustrates one embodiment of a computer-implemented method that may be used to determine the optimal parameters for inspection of a specimen. The method may be used to automatically enhance the inspection of selected defects such as low contrast defects. Existing methods for determining parameters for inspection generally include tedious manual set up and tool optimization. Therefore, such methods are generally time consuming and inaccurate. The methods described herein, however, may be used for automatically determining and optimizing the parameters for inspection. As such, the methods described herein may be faster and easier to use. In addition, the automatic selection scheme may be used for numerous inspection parameters to optimize detection of defects of a particular type such as relatively low contrast defects. Furthermore, inspections that are optimized by defect type may provide more useful results to the user.

As used herein, the term "specimen" refers to either a wafer or a reticle. The wafer may be a wafer at any stage of a semiconductor fabrication process including a virgin wafer and a completed wafer. In a similar manner, the reticle may be a reticle at any stage of a reticle fabrication process or a completed reticle that may or may not be released for use in a semiconductor fabrication facility. The term "specimen" also includes a surface or a substrate as defined above. As used herein, the term "optimal parameters" refers to parameters that if used for inspection of a specimen would have a higher detection rate for at least one type of defect than other parameters.

The computer-implemented method includes determining optimal parameters for inspection of a specimen based on defects selected for detection on the specimen, as shown in step 801. The optimal parameters may include, but are not limited to, an optimal illumination wavelength, an optimal illumination polarization, an optimal angle of incidence, an optimal illumination light level, an optimal numerical aperture, an optimal collection angle, an optimal image processing algorithm, an optimal threshold for defect detection, etc. In general, the optimal parameters may include any parameters of an inspection system that may be altered. In addition, the optimal parameters may include one parameter or a combination of parameters. In one embodiment, the optimal illumination wavelength may be determined as described above based on the optical characteristics of the specimen at various wavelengths.

In some embodiments, the defects may be selected by a user. According to another embodiment, the defects may include relatively low contrast defects. For example, the defects of interest may be "stringers." Stringers are generally defined as hard to find defect types, which are artifacts of insufficient over-etch time in etch processes, and particularly anisotropic etch processes. Stringers may include portions of the etched film remaining after the etch process, typically along edge steps in the specimen topography.

Determining the optimal parameters may include performing one or more test inspections of a specimen with different parameters, as shown in step 803. The specimen that is used for the test inspections may be the specimen that will ultimately be inspected using the optimal parameters. Alternatively, the specimen that is used for the test inspections may be a test specimen, which is known to have one or more of the selected defects. In one embodiment, the test inspections may be carried out as described above with respect to determining the optimal inspection wavelength(s) in the opaque and/or transmissive regimes. Other test inspections may be performed in a similar manner with other parameters.

Determining the optimal parameters may also include identifying which of the different parameters, used in the test inspections, produces the largest capture rate of the selected defects, as shown in step 805. In some embodiments, determining the optimal parameters may include determining which of the different parameters produces the largest capture rate of the selected defects without increasing the number of false defects that are detected. In one embodiment, identifying which of the different parameters produces the largest capture rate may include classifying defects detected during the one or more test inspections, as shown in step 807. In a different embodiment, identifying which of the different parameters produces the largest capture rate may include automatically classifying defects detected during the one or more test inspections.

In one particular embodiment, a defect having particular characteristics may be selected by a user. The defect's characteristics may be part of a classification scheme such as that described in International Publication No. WO 01/40145 A2 by Baker et al., which is incorporated by reference as if fully set forth herein. Classification may also be performed using an automatic defect classification (ADC) scheme such as that included in one of the iADC products commercially available from KLA-Tencor, San Jose, Calif. Inspection of a specimen may be carried out, and the parameters may be optimized during classification so that the capture rate of the selected defect type may be increased, and preferably maximized. This rate may also be maximized by inspecting a wafer known to have defects having the characteristics selected by the user. Alternatively, a product wafer may be inspected while varying the parameters of the inspection so that defects of interest are found at an increasing rate without increasing the false defect count. Determining the different capture rates may be performed, for example, by grouping classified defects using the Kohonen mapping technique, which is known in the art. The rate at which defects at a point of interest on a Kohonen map increase relative to those points on the map which are of less interest may be determined. If the parameters of the inspection are set so that only the points of interest on the map increase, then it is relatively likely that the sensitivity of the inspection to that particular defect type has increased.

The method also includes setting parameters of an inspection system at the optimal parameters prior to the inspection of the specimen, as shown in step 809. The inspection system may then be set up in a way that optimizes capture of the particular defects of interest. In one embodiment, the optimal parameters may result in more of the selected defects being detected during the inspection than that which would be detected using other parameters. In another embodiment, the optimal parameters may result in fewer non-selected defects being detected during the inspection than that which would be detected using other parameters. In an additional embodiment, the optimal parameters may result in a number of false defects detected during the inspection that is equal to or less than that which would be detected using other parameters.

Setting the parameters may be performed by a computer system or a processor, which may be configured as described herein. The computer system or the processor may be coupled to various components of the inspection system via suitable electronic components. For example, a computer system may be coupled to a light source, an adjustable aperture, and a detection subsystem of the inspection system via appropriate electronic components. In this manner, the computer system or the processor may alter one or more parameters of various components of the inspection system depending upon the optimal parameters. The method may include any other steps of any other methods described herein.

Program instructions implementing methods such as those described above may be transmitted over or stored on a carrier medium. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

Currently, defect detection on semiconductor wafers with DUV light may be performed with either a broadband illumination source such as an arc lamp or a monochromatic light source such as a laser. One disadvantage for wafer inspection systems that utilize a broadband illumination source is that the broadband illumination source does not provide sufficient energy for the DUV region. In addition, the optical subsystem for performing wafer inspection in the DUV region with broadband illumination is relatively difficult to design and manufacture because of the limitations in the materials available for the optical components.

The optical subsystem for a wafer inspection system that includes a monochromatic illumination source is easier to design and manufacture in comparison to the DUV broadband system. However, because of the monochromatic nature of the illumination source, the color noise may be excessive for certain wafers such as back end of the line (BEOL) wafers. Furthermore, because such systems utilize only one wavelength, such systems will not be able to provide sufficient defect contrast for a wide range of wafer materials and structures such as gate-to-gate bridging structures. This inability for sufficient defect contrast becomes more important when the inspection illumination is shifted toward DUV because the material properties usually change significantly in the shorter wavelength region.

Figure 9:
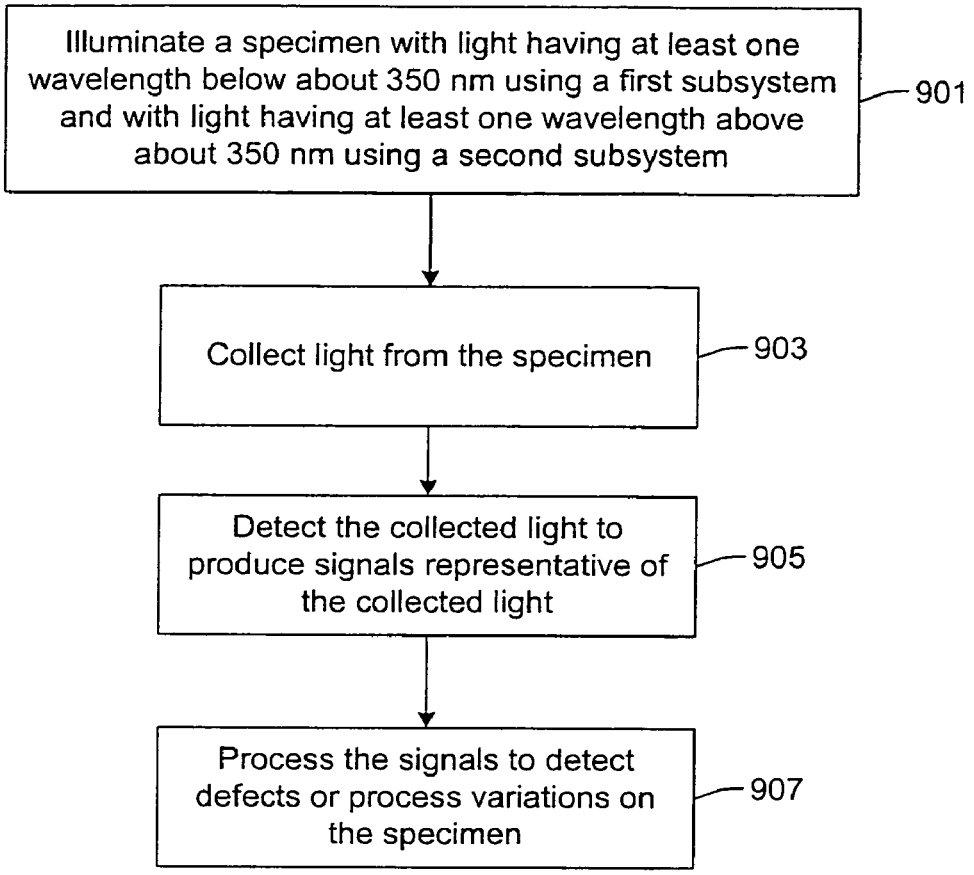
FIG. 9 is a flow diagram illustrating another embodiment of a method for inspecting a specimen.

FIG. 9 illustrates an additional embodiment of a method for inspecting a specimen that overcomes many of the problems of DUV inspection described above. This method involves using multiple illumination sources integrated into an inspection system. The multiple illumination sources may provide at least one DUV spectrum. In addition, the inspection system may have a "superset" capability that allows operation at a specific illumination/collection mode or a combination of the inspection modes to provide substantially complete inspection for any specimen layer, structure, and/or defect. As used herein, the term "mode" generally refers to a parameter selection (e.g., a spectrum selection, a polarization selection, etc.). In this manner, the inspection system may have the capability for achieving the best defect contrast for any given specimen structure. In addition, the methods described herein will provide better defect detection capability for any inspection system that utilizes a DUV spectrum.

In one embodiment, at least a portion of a surface of the specimen may include polysilicon, single crystal silicon, silicon dioxide, silicon nitride, or any combination thereof. In addition, at least a portion of the specimen may include any other materials described herein. Since the inspection method described herein provides multiple mode inspection, the inspection methods may be advantageously used to inspect a wide variety of materials with sufficient energy and defect contrast.

The method includes illuminating the specimen with light having at least one wavelength below about 350 nm using a first subsystem and with light having at least one wavelength above about 350 nm using a second subsystem, as shown in step 901. In some embodiments, illuminating the specimen may include illuminating the specimen using the first and second subsystems substantially simultaneously. In other embodiments, illuminating the specimen may include illuminating the specimen using the first and second subsystems at different times. For example, the first and second subsystems may be operated independently of one another. The first and second subsystems may be optimized for each of the at least one wavelength below and above about 350 nm, respectively.

In one embodiment, the first subsystem may include a laser. In another embodiment, the second subsystem may include a laser. In some embodiments, the first and second subsystems may include a common laser. For example, the common laser may include a multi-wavelength laser device such as a neodymium YAG laser. In a different embodiment, the first subsystem may include a first laser, and the second subsystem may include a second laser. The first laser may be configured to produce light having a wavelength below about 350 nm, and the second laser may be configured to produce light having a wavelength above about 350 nm. In other embodiments, the second subsystem may include a polychromatic light source. For example, the second subsystem may include an arc lamp. In some embodiments, the first and second subsystems may include a common polychromatic light source. In other embodiments, the first subsystem may include a first polychromatic light source, and the second subsystem may include a second polychromatic light source. The first polychromatic light source may be configured to produce light having a wavelength below about 350 nm, and the second polychromatic light source may be configured to produce light having a wavelength above about 350 nm. The first and second subsystems may be further configured as shown in and described with respect to FIGS. 4a, 5, 6, and 10. A laser or a polychromatic light source may include any of the lasers or polychromatic light sources described herein.

Illuminating the specimen may be performed as described above using a "superset" inspection system that includes more than one illumination source, including at least one illumination source that provides light within the DUV region. Each illumination subsystem may also be configured with various modes (e.g., various aperture illumination modes, various polarization modes, etc.) that are appropriate for the types of illumination sources. An inspection system that may be used to perform the methods described herein may include the subsystems and light sources described herein and may further have one of the following possible configurations. For example, the inspection system may include at least one monochromatic source to provide DUV illumination and at least one arc lamp source to provide illumination above about 350 nm. Alternatively, the inspection system may include two or more monochromatic light sources that can provide illumination above and below about 350 nm. In a further alternative, the inspection system may include two or more polychromatic light sources that can provide illumination above and below about 350 nm. The inspection system may be further configured as described herein.

Inspection of a specimen may be performed using any of the combinations of light sources substantially simultaneously or independently. In addition, the optical subsystem for any of the light sources described above may have the capability to provide variable coherent illumination and variable pupil illumination profiles such as ring illumination. If the light source is monochromatic, the optical subsystem may also provide dark field illumination capability. For this type of light source, the illumination subsystem may also be constructed to provide adjustable polarization modes. For example, the illumination subsystem may include one or more polarization filters and/or waveplates.

The method also includes collecting light from the specimen, as shown in step 903. Light from the specimen may be collected using an objective or another suitable optical component or subsystem described herein or known in the art. In one embodiment, the collected light may include a bright field image of at least a portion of the specimen. In some embodiments, the collected light may include optical phase signals. In addition, the method includes detecting the collected light to produce signals representative of the collected light, as shown in step 905. Detecting the collected light may be performed using any of the detection subsystems described herein. The detection subsystem for each of the above light sources may have some common, shared components or may have completely separate optical components. If the light sources of the first or second subsystem provide alterable polarization modes, then the detection subsystems may also be configured for detecting and/or imaging with variable polarization states. For example, one or more polarization filters may be coupled to the detection subsystems such that the polarization of the light that is detected and/or imaged by the detection subsystems may be altered. In one embodiment, at least the one wavelength of the second subsystem may be selected to increase contrast in the signals for a material of the specimen. In addition, at least the one wavelength of the first subsystem may be selected to increase sensitivity to the defects. Selection of the wavelength(s) for the first and second subsystems may be performed as described above.

The method further includes processing the signals to detect defects or process variations on the specimen, as shown in step 907. Processing the signals may be performed as described above. In one embodiment, the first subsystem may include a dark field illumination source. For example, a light source of the first subsystem may be a monochromatic or near-monochromatic light source. In one such embodiment, processing the signals may include Fourier filtering the signals corresponding to the collected light resulting from illuminating the specimen using the first subsystem. Fourier filtering may be performed using any method known in the art. This method may also include any other steps of any other methods described herein.

A further embodiment relates to a different method for inspecting a specimen. The method includes illuminating the specimen. In one embodiment, illuminating the specimen may include illuminating the specimen with light having at least one wavelength below about 350 nm and illuminating the specimen with light having at least one wavelength above about 350 nm. Illuminating the specimen may be performed as described above. In addition, illuminating the specimen may be performed in this method using any of the embodiments of the inspection systems or subsystems described herein. The method also includes collecting light from the specimen. Collecting the light from the specimen may be performed as described above.

In addition, the method includes detecting the collected light to produce optical phase signals representative of a first portion of the collected light and brightfield optical signals representative of a second portion of the collected light. For example, the collected light may be separated into the different portions by an optical component such as a beamsplitter. The different portions of light may then be directed to different detection subsystems. The detection subsystems and the beamsplitter may be configured as described herein. The optical phase signals may correspond to thin film optical properties of the specimen, particularly, if at least a portion of the specimen is relatively transmissive at one or more of the illumination wavelengths as further described in more detail above. For example, the first portion of the collected light may result from illumination of the specimen with light having at least one wavelength below about 350 nm. If the specimen or a portion of the specimen is at least partially transmissive at such wavelengths, then signals corresponding to the first portion of the collected light may be optical phase signals. In contrast, the brightfield optical signals may be caused by diffraction and scattering from the specimen, particularly, if at least a portion of the specimen is relatively opaque at one or more of the illumination wavelengths as described in more detail above. For example, the second portion of the collected light may result from illumination of the specimen with light having at least one wavelength above about 350 nm. If the specimen or a portion of the specimen is relatively opaque at these wavelengths, then signals corresponding to the second portion of the collected light may be brightfield optical signals.

The method further includes processing the optical phase signals and the brightfield optical signals separately to detect defects or process variations on the specimen. For example, since the optical phase signals and the brightfield optical signals may be produced by different detection subsystems, the optical phase signals and the brightfield optical signals may be easily processed by separate circuitry or units of a processor or computer system. The processor or computer system may be configured as described herein. As described further above, the different signals resulting from the different modes of illumination may provide improved defect detection. This method may also include any other steps of any other methods described herein. The method may also be performed using any of the embodiments of inspection systems or subsystems described herein (e.g., the embodiments shown in FIGS. 4a, 5, 6, 10, 12, 15(a), 15(b), 16(a), and 16(b)).

Additional embodiments relate to inspection systems configured to have improved illumination efficiency and to allow efficient illumination with more than one illumination source. Currently, inspection systems typically utilize broadband illumination that is based on a mercury lamp or narrow-band illumination that is laser based. A typical wafer inspection system may also have a relatively small pixel size at the wafer with a high magnification imaging system. Such a configuration results in a relatively small wafer field. In addition, some wafer inspection systems have more than one magnification setting. Such a configuration results in a variable wafer field size. Furthermore, some currently available wafer inspection systems have the capability for high numerical aperture (NA) illumination for incoherent imaging or the capability for edge illumination or pupil filtering. In order to provide the above features, the illumination system of such inspection systems is configured to deliver sufficient radiance to the wafer that has a relatively small optical invariant, a variable optical invariant, and a variable illumination pupil distribution.

Currently, lamp-based illumination systems for UV/DUV inspection systems are either refractive element-based condenser systems or reflector-based systems that include an ellipsoidal mirror. One problem with refractive element-based condenser systems is that the color correction of such elements is generally not sufficient for DUV applications because the material selection is limited to fused silica and calcium fluoride. One problem for ellipsoidal reflector designs is that they produce an aberrated image of the arc lamp that is not easily coupled into an illumination system with a relatively small optical invariant that requires high radiance. It is also not ideal to utilize lamp-based illumination subsystems in combination with laser light sources because of the differences in optical invariant between these two sources. For example, a lamp source has a relatively large optical invariant, while a laser source has a relatively small optical invariant.

Several of the method and system embodiments described herein, however, utilize more than one type of illumination source. These systems may be configured to provide a highly efficient illumination system for UV/DUV inspection systems. For example, an inspection system may include one or more of the optical subsystems described below.

Figure 10:
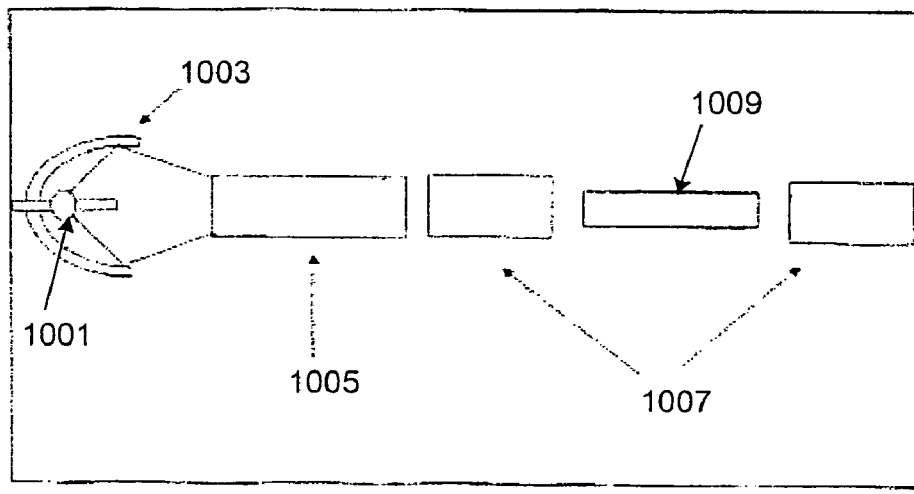
FIG. 10 is a schematic diagram illustrating one embodiment of a first optical subsystem, which may be coupled to a broadband light source in an inspection system.

In one embodiment, a system configured to inspect a specimen includes a first optical subsystem coupled to a broadband light source. One example of a first optical subsystem is shown in FIG. 10 coupled to broadband light source 1001. The broadband light source may be configured to generate visible light, UV light, DUV light, or a combination thereof. The broadband light source may include any broadband light source described herein such as an arc lamp.

Figure 11A:
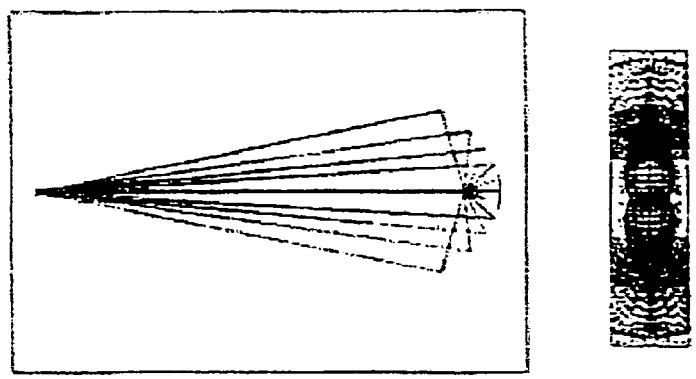
FIGS. 11(a) and 11(b) are schematic diagrams illustrating images of a cathode at a second focal plane produced by ellipsoidal mirrors having different eccentricities.
Figure 11B:
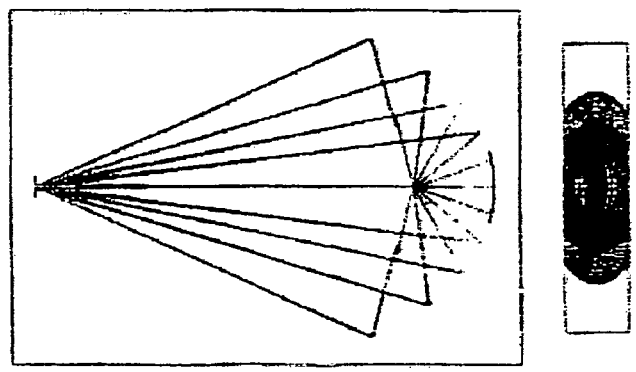

In an embodiment, the first optical subsystem may include ellipsoidal mirror 1003. Using an ellipsoidal mirror for an extended source may be problematic because the magnification of the source for any given ray trace is dependent on the ratio of the distance from the intersection of the mirror to the second focal point and the distance from the intersection of the mirror to the first focal point. For an ellipsoidal mirror with relatively large eccentricity, this ratio is strongly dependent on the ray angle for any source point that is not at the first focal point. For example, FIGS. 11(a) and 11(b) illustrate the imaged spot produced by two ellipsoidal mirrors having different eccentricities for a source that extends about 1×1 mm. FIG. 11(a) is an image of a cathode at a second focal plane with an ellipsoidal mirror that has a relatively large eccentricity. FIG. 11(b) is an image of a cathode at a second focal plane with an ellipsoidal mirror that has a relatively small eccentricity.

Therefore, if ellipsoidal mirror 1003 has less eccentricity than commonly used ellipsoidal mirrors, it may produce a less aberrated image of the cathode of the broadband light source. As such, ellipsoidal mirror 1003 may be configured to produce a substantially aberration-free image of the broadband light source. In addition, the ellipsoidal mirror may be configured to provide substantially efficient coupling of light from the broadband light source to a third optical subsystem.

In this manner, the ellipsoidal mirror may provide higher coupling of the broadband light source energy into the inspection system.

In some embodiments, the first optical subsystem may also include beam shaping element 1005, as shown in FIG. 10. The beam shaping element may be an axicon that is reverse-oriented. In one embodiment, the beam shaping element may be configured to direct edge radiance of the broadband light source to a central portion of a pupil of the first optical subsystem. Such a beam shaping element may be advantageous for brightfield illumination. For example, the beam shaping element may be configured to "repair" the center obstruction created by the reflector for full NA bright field illumination. In another embodiment, the beam shaping element may be configured to alter a beam profile of the broadband light source such that the beam profile is substantially uniform. In some embodiments, the beam shaping element may be configured to provide beam shaping for oblique illumination. The beam shaping element may be moved out of the location in the first optical subsystem shown in FIG. 10 to provide edge illumination by the ellipsoidal mirror. Edge illumination may be used for edge contrast mode inspection or eclipse mode inspection.

One of the challenges for an illumination system used for inspection applications is that the optical invariant varies significantly from one magnification setting to another. Conventional zooming will not vary the optical invariant. Therefore, conventional zooming will not provide a good match for the optical invariant at a wide range of magnification settings. In one embodiment, the first optical subsystem may include double zooming element 1007 configured to alter an optical invariant of the broadband light source. For example, the double zooming element may provide proper matching of the illumination to the appropriate optical invariant for inspection. In some embodiments, the first optical subsystem may include light pipe 1009, which may be disposed between individual zooming elements of the double zooming element. The light pipe may be configured to homogenize the spatial intensity distribution of the broadband light source. With the additional zooming capability in front of the light pipe (integrator), it is possible to modify the optical invariant that is delivered to the specimen to match the inspection setting. The zooming element in front of the light pipe will alter the imaging spot projected at the entrance port and may affect the coupling efficiency. However, since it is not possible to achieve 100% coupling of the broadband light source radiance to the light pipe, it is preferable to eliminate any loss after the light pipe and to shift the illumination shaping in front of the light pipe.

The system also includes a second optical subsystem (not shown) coupled to a laser (not shown). The second optical subsystem may include a number of optical components such as a homogenizer, a beam expander, a beam shaping element, a polarization filter, a folding mirror, a lens, and a deflector. The second optical subsystem may also include any other appropriate optical components known in the art. In one embodiment, the laser may be configured to generate light having a wavelength less than about 350 nm. In a different embodiment, the laser may be configured to generate light having a wavelength less than about 266 nm. In this manner, the laser may be configured to generate UV or DUV light.

In addition, the system may include an efficient illumination insertion module that will allow highly efficient coupling of laser illumination to an objective for simultaneous operation and inspection with the spectrums of the laser and the broadband light source. In this manner, the illumination insertion module can accommodate both of the illumination sources. For example, the illumination insertion module may include a third optical subsystem configured to couple light from the first and second optical subsystems to an objective. Preferably, the third optical subsystem may also be configured to allow substantially efficient coupling of the light from the second optical subsystem to the objective. The objective is configured to focus the light onto the specimen. In one embodiment, the objective may also be configured to illuminate the specimen with light from the first and second optical subsystems substantially simultaneously. The objective may include a single lens or a compound lens. In addition, the objective may be formed of a single refractive material or of different refractive materials. The objective may be further configured as described above.

Figure 12:
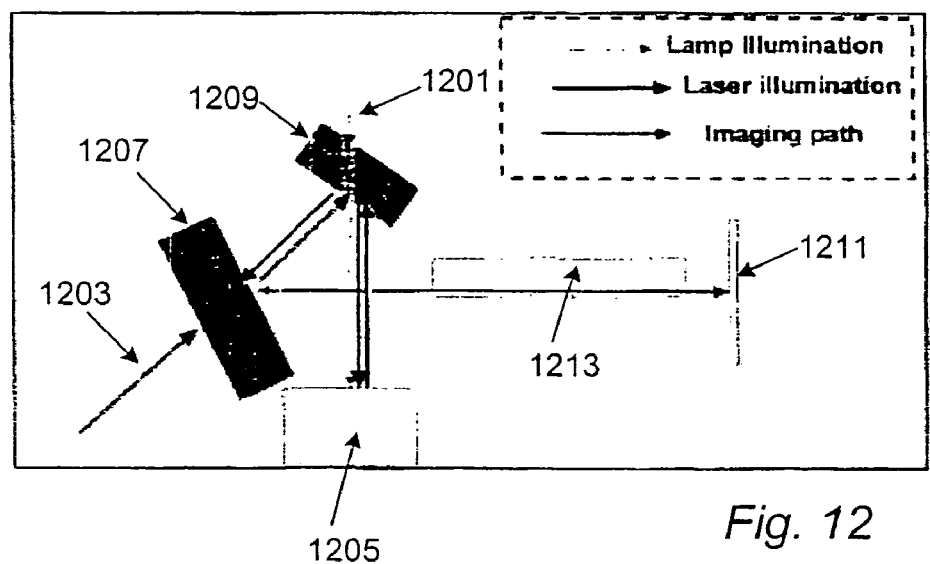
FIG. 12 is a schematic diagram illustrating one embodiment of a third optical subsystem, which may be configured to couple light from two optical subsystems to an objective.

One embodiment of a third optical subsystem is illustrated in FIG. 12. The third optical subsystem may be configured to couple light 1201 from the first optical subsystem and light 1203 from the second optical subsystem to objective 1205. As described above, the first optical subsystem is coupled to a broadband light source, and the second optical subsystem is coupled to a laser. In some embodiments, the third optical subsystem may include polarization beamsplitter 1207, which is configured to direct the light from the second optical subsystem to dichroic beamsplitter 1209. Polarization beamsplitter 1207 may also function as a dichroic beamsplitter in some embodiments. Dichroic beamsplitter 1209 may be configured to direct the light from the second optical subsystem to the objective. In one embodiment, dichroic beamsplitter 1209 may also be configured to direct at least a portion of the light from the first optical subsystem to the objective. For example, dichroic beamsplitter 1209 may be a 50/50 dichroic beamsplitter that will transmit about 50% of the broadband light source spectrum. In addition, the 50/50 dichroic beamsplitter may be configured to reflect the laser spectrum that is at one end of the imaging spectrum such that it is also directed to the objective.

In addition, the system includes detection subsystem 1211 configured to detect light from the specimen and to produce signals representative of the detected light. In some embodiments, the light from the specimen may first pass through the objective to the dichroic beamsplitter, which may direct the light from the specimen to the polarization beamsplitter. The polarization beamsplitter may also be configured to direct the light from the specimen to the detection subsystem. In some embodiments, the system may include zooming element 1213 coupled to the detection subsystem, as shown in FIG. 12. The zooming element may be configured to alter the magnification setting of the detection subsystem. Furthermore, the system may include a processor (not shown) configured to process the signals to detect defects or process variations on the specimen. The system may be further configured as described herein.

In the system described above, therefore, the illumination subsystems are configured to deliver the largest optical invariant for inspection with little adjustment to the system, to change the optical invariant delivered to the specimen, and to change the illumination pupil profile for different modes of operation. In addition, the system has several features that will substantially improve the illumination efficiency for inspection systems that are operated with DUV illumination. Furthermore, the system will improve the coupling of laser illumination and lamp based illumination to the imaging objective.

Additional embodiments relate to UV/DUV inspection systems that are configured to have enhanced defect detection capability. Currently, UV/DUV inspection systems typically use an illumination spectrum below about 400 nm. The illumination source can be lamp- or laser-based. An inspection system with a broadband illumination system can be operated at either a broadband region or a sub-band region. Typically, broadband inspection is used for best throughput while narrow-band illumination or sub-band regions are used for optimal sensitivity and detection performance. For example, broadband mode provides the best throughput, but detection sensitivity of the broadband mode is sometimes reduced relative to narrow-band detection. A disadvantage of current inspection systems is that they can operate either in broadband mode or narrow-band mode, but inspection cannot be performed with both modes simultaneously. In addition, if the inspection system is operated in narrow-band mode, it may be necessary to process a single wafer more than once at different wavelength settings.

Figure 13:
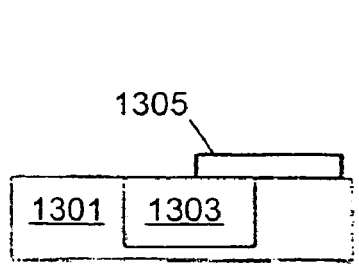
FIG. 13 is a schematic diagram illustrating a cross-sectional view of one example of a specimen.
Figure 14:
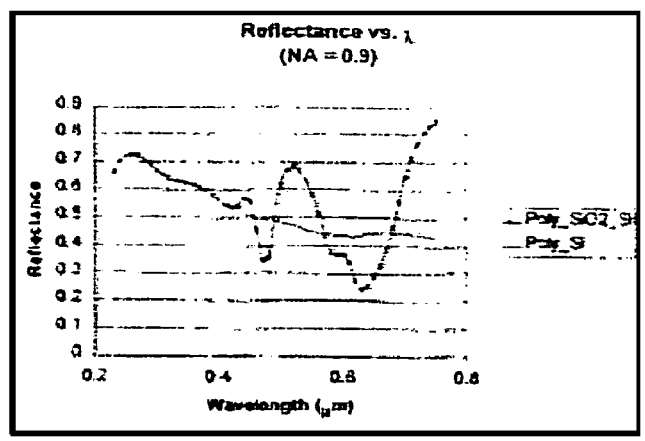
FIG. 14 is a plot illustrating reflectance for various materials at various wavelengths.

As described above, the optical properties of materials typically used in wafer manufacturing change significantly as the spectrum is shifted toward the UV and DUV ranges. In addition, a specimen may include several different types of materials. For example, as shown in FIG. 13, a specimen, which in this case is a wafer, may include single crystal silicon substrate 1301 in which a $SiO_2$ shallow trench isolation (STI) trench 1303 is formed. In addition, polysilicon structure 1305 may be formed on the specimen. As shown in FIG. 13, the polysilicon structure may be formed over the STI trench and the single crystal silicon substrate. However, the polysilicon structure may be arranged over a different portion of the specimen (e.g., arranged entirely over the single crystal silicon substrate). The specimen may also include other materials described herein. Therefore, as different portions of the specimen are scanned, the optical properties of the specimen will change depending on the wavelength of illumination and the material(s) located in those different portions. For example, FIG. 14 is a plot illustrating reflectance for polysilicon and a polysilicon/$SiO_2$/single crystal silicon stack at various wavelengths. As shown in FIG. 14, the differences in contrast between polysilicon and a polysilicon/$SiO_2$/single crystal silicon stack are significantly reduced for illumination below about 400 nm. Therefore, inspection involving polysilicon may be difficult below about 400 nm. However, the inspection may be optimized using illumination within the visible spectrum. Other materials, structures, and defect types may be best inspected at shorter wavelengths.

One advantage of the systems and methods described herein is that the detection capabilities and flexibility for UV/DUV inspection systems and methods are increased. For example, the illumination and imaging spectrums may be extended to the visible range with one or more illumination and/or detection subsystems that can be operated either substantially simultaneously or independently at different times within the UV/DUV inspection system. A benefit of extending the inspection spectrum of UV/DUV inspection systems is demonstrated in FIGS. 13 and 14, which illustrates one type of wafer structure that has substantially low contrast in the UV/DUV range but exhibits greater signal in the visible region. In one embodiment, the inspection spectrum of a broadband DUV inspection system may be extended by modifying the system or adding additional illumination and/or detection subsystems such that the system can be operated in the visible range (e.g., from about 248 nm to about 450 nm). One example of a broadband DUV inspection system that can be used for inspection in both the UV/DUV and visible ranges is illustrated in U.S. Pat. No. 6,392,793 B1 to Chuang et al., which is incorporated by reference as if fully set forth herein. An inspection system configured for inspection in the UV/DUV and visible ranges may also be configured according to any of the embodiments described herein.

In one embodiment, a system may include a first illumination subsystem, which is configured to illuminate the specimen with light having a wavelength less than about 350 nm. The system may also include a second illumination subsystem configured to illuminate the specimen with light having a wavelength greater than about 350 nm. The first and second illumination subsystems may have different and/or independently variable illumination apertures. In one embodiment, the first and second illumination subsystems may be configured to illuminate the specimen in a narrow-band mode. In a different embodiment, the first illumination subsystem may be configured to illuminate the specimen in a narrow-band mode while the second illumination subsystem may be configured to illuminate the specimen in a broadband mode. In some embodiments, the first and second illumination subsystems may be configured to illuminate the specimen substantially simultaneously. The first and second illumination subsystems may be further configured as described herein.

In an embodiment, the system includes a first detection subsystem configured to detect a first portion of light from the specimen. In addition, the system includes a second detection subsystem configured to detect a second portion of light from the specimen. The first portion of light and the second portion of light may have at least one different characteristic. The different characteristics may include, for example, different wavelengths or different polarizations. In some embodiments, the first and second detection subsystems may have different magnification settings. For example, the first portion of light, which is detected by the first detection subsystem, may be produced by illuminating the specimen using the first illumination subsystem. In such an embodiment, the first detection subsystem may have a magnification setting that is higher than a magnification setting of the second detection subsystem. In one embodiment, the first and second detection subsystems may be configured to detect the first and second portions of light substantially simultaneously.

In this manner, the inspection system may include more than one sensor so that it can detect more than one illumination mode in one inspection scan. The illumination modes can be different spectrum bands, different polarization modes, or different illumination aperture modes. In addition, the detection subsystems may be operated at more than one magnification setting. One advantageous configuration is to direct longer wavelengths to the low magnification setting and shorter wavelengths to the high magnification setting so that inspection can be performed at the optimal pixel sampling for each range of wavelengths.

Figure 15A:
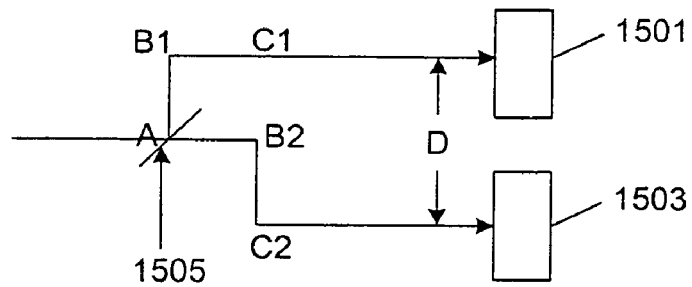
Figure 15B:
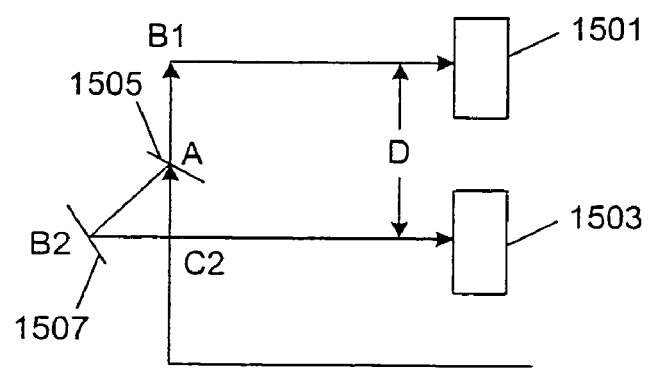

FIGS. 15(a) and 15(b) illustrate different embodiments of first and second detection subsystems that may be included in an inspection system to provide multiple mode detection. In both embodiments, the detection subsystems may include two or more detection sensors 1501, 1503 that are spaced apart in the imaging plane by a distance, D. The detection sensors may include any of the detection sensors described herein or known in the art. The detection subsystems also include one or more mode separation elements that are configured to direct one mode along one path to one of the detection sensors while directing another mode along a different path to the other detection sensor. For example, as shown in FIGS. 15(a) and 15(b), the mode separation elements may include beamsplitter 1505. The beamsplitter may be a dichroic beamsplitter that is configured to separate light from the specimen into two portions that have different wavelengths. Alternatively, the beamsplitter may be a polarization beamsplitter that is configured to separate light from the specimen into two portions that have different polarizations. The different polarizations may be orthogonal to one another. The beamsplitter may preferably be located after any alignment mechanism to minimize duplicate hardware. The detection subsystems may further include path equalization and re-direction elements that will re-direct the separated beams to the appropriate detection sensors and maintain the optical path for image formation. For example, as shown in FIG. 15(b), the detection subsystems may include path re-direction element 1507, which is configured to direct one portion of the light separated by beamsplitter 1505 to detection sensor 1503. In some embodiments, the path equalization and re-direction elements may include folding mirrors, beamsplitters, or any other appropriate optical components known in the art. Additional path equalization and re-direction elements (not shown) may also be placed at locations B1, B2, and C2 shown in FIG. 15(a) and at location B2 shown in FIG. 15(b). In FIG. 15(a), the distance from A to B1 to C1 may be approximately equal to the distance from A to B2 to C2. In FIG. 15(b), the distance from A to B1 may be approximately equal to the distance from A to B2 to C2.

One of the challenges for a broadband visible/UV/DUV inspection system is to maintain the optimal pixel sampling for substantially different spectrums. To alleviate this problem, one embodiment of an inspection system may include a detection subsystem that includes multiple zooming elements that have different or independently variable magnifications. Each of the multiple zooming elements may be operated at a setting with a broad magnification range. One example of an inspection system that may be configured to have different zooming elements is illustrated in U.S. Pat. No. 6,392,791 B1 to Chuang et al., which is incorporated by reference as if fully set forth herein.

FIGS. 16(a) and 16(b) also illustrate different embodiments of detection subsystems that include multiple zooming elements. As shown in FIGS. 16(a) and 16(b), light from the specimen may be collected by objective 1601. Objective 1601 may be configured to direct the light to pupil relay lens 1603. As further shown in FIGS. 16(a) and 16(b), the pupil relay lens may be configured to direct the light to beamsplitter 1605. The beamsplitter may be configured to separate the light into two different beams having different characteristics (e.g., wavelength, polarization, etc.). One of the beams may be directed to low magnification zooming element 1607 while the other beam is directed to high magnification zooming element 1609. Both of the zooming elements may be optically coupled to detection sensors (not shown). As shown in FIG. 16(a), the detection subsystems may not include optical components between the beamsplitter and the zooming elements. Alternatively, as shown in FIG. 16(b), the detection subsystems may include one or more optical components 1611 disposed between the beamsplitter and one or more of the zooming elements. Optical component 1611 shown in FIG. 16(b) may be a folding mirror or any other suitable optical component known in the art.

Longer wavelengths of the collected light may be directed to the lens magnification zooming element while shorter wavelengths of the collected light may be directed to the high magnification zooming element. For example, FIG. 17 illustrates field coverage of specimen 1701 and corresponding TDI images 1703. As shown in FIG. 17, the signals corresponding to illumination at a wavelength of 266 nm may be directed to the TDI at a magnification (200×) higher than that at which the signals corresponding to illumination at a wavelength of 436 nm are directed to the TDI (100×). The different wavelengths of light may be directed to different portions of the same TDI. FIG. 18 illustrates one path arrangement for a detection subsystem configured such that images of a specimen can be directed to any portion of the TDI. For example, one of optical components 1801 may be adjusted axially to form an image of the specimen at a different location on the detector. In some embodiments, the optical components may include folding mirrors or any other suitable optical component.

One of the challenges for a broadband visible/UV/DUV inspection system relates to the anti-reflection coating design that is used to cover such a broad spectrum range. It may, thus, be beneficial to implement through-the-lens auto-focus for such inspection systems. The auto-focus may be operated at one or more wavelengths closer to the imaging spectrum to allow a higher efficiency anti-reflection coating design. For example, in some embodiments, the system may also include an auto-focus subsystem (not shown) configured to operate at wavelengths within about 80 nm of the wavelength of the imaging spectrum (e.g., within about 80 nm of the wavelength greater than about 350 nm).

Furthermore, the system may include a processor (not shown) configured to process signals produced by the first and second detection subsystems to detect defects or process variations on the specimen. The processor may be configured to process the signals as described above. The processor may be coupled to the detection sensors or suitable electronics that are coupled to both the processor and the detection sensors. The processor may include any suitable processor or computer system known in the art. The system may be further configured as described herein.

In an embodiment, a processor or computer system may be configured to execute the program instructions to perform finctions and/or a computer-implemented method according to the above embodiments. The computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The systems described above will surpass the detection capabilities of existing UV/DUV inspection systems. For example, the inspection systems described herein add visible spectrum capability to UV/DUV inspection systems. In addition, existing inspection systems use only a single imaging system and, therefore, may be optimized for only a single mode at any point in time. Therefore, when more than one mode of narrow-band inspection is used for a single specimen, an existing inspection system must perform a new inspection process for each mode. The systems described herein, however, incorporate multiple detection subsystems, and each detection subsystem may be optimized for a different mode. As such, the inspection systems described herein allow multiple inspection modes to be performed simultaneously, thus eliminating the need to perform an inspection process for each mode. Furthermore, the systems described herein allow simultaneous operation at more than one magnification setting.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. In particular, it is contemplated by the inventors that embodiments using a wide range of lasers, polychromatic sources (e.g., arc lamps), and other illumination devices are within the scope of this patent. Moreover, the inventor contemplates that the principles of the present invention can be practiced with substrates have a wide range of opacity transition wavelengths. Further, reference in the claims to an element in the singular is not intended to mean "one and only one" unless explicitly stated, but rather "one or more." Furthermore, the embodiments illustratively disclosed herein can be practiced without any element which is not specifically disclosed herein.

What is claimed is:

1. A computer-implemented method, comprising:
    determining optimal parameters for inspection of a specimen based on defects selected for detection on the specimen, wherein the optimal parameters result in a number of false defects detected during the inspection equal to or less than that which would be detected during the inspection using other parameters, wherein the optimal parameters result in fewer non-selected defects being detected during the inspection than that which would be detected during the inspection using the other parameters, wherein the selected defects have a defect type different than the defect type of the non-selected defects, and wherein the non-selected defects comprise defects other than false defects; and
    setting parameters of an inspection system at the optimal parameters prior to the inspection of the specimen, wherein the inspection comprises scanning the specimen with the inspection system.

2. The method of claim 1, wherein the optimal parameters result in more of the selected defects being detected during the inspection than that which would be detected during the inspection using the other parameters.

3. The method of claim 1, wherein the defects are selected by a user.

4. The method of claim 1, wherein said setting is performed by a computer.

5. The method of claim 1, wherein the selected defects comprise relatively low contrast defects.

6. The method of claim 1, wherein said determining comprises performing one or more test inspections of the specimen with different parameters and identifying which of the different parameters produces the largest capture rate of the selected defects.

7. The method of claim 6, wherein said identifying comprises classifying defects detected during the one or more test inspections.

8. The method of claim 6, wherein said identifying comprises automatically classifying defects detected during the one or more test inspections.

9. The method of claim 6, wherein said determining further comprises determining which of the different parameters produces the largest capture rate of the selected defects without increasing the number of the false defects that are detected.

10. The method of claim 1, wherein said determining comprises performing one or more test inspections of a test specimen, known to have one or more of the selected defects, with different parameters and identifying which of the different parameters produces the largest capture rate of the selected defects.

11. The method of claim 1, wherein the specimen is a wafer or a reticle.

12. The method of claim 1, wherein the optimal parameters comprise illuminating the specimen with at least one wavelength below about 350 nm and at least one wavelength above about 350 nm.

13. The method of claim 1, wherein the optimal parameters comprise illumination of the specimen with at least one wavelength selected to increase contrast in signals for a material of the specimen and at least one wavelength selected to increase sensitivity to the selected defects.

14. The method of claim 1, wherein the inspection comprises collecting light from the specimen, detecting the collected light to produce optical phase signals representative of a first portion of the collected light and brightfield optical signals representative of a second portion of the collected light, and processing the optical phase signals and the brightfield optical signals separately to detect the selected defects on the specimen.

15. The method of claim 1, wherein the specimen is characterized by an opacity transition wavelength, and wherein the optimal parameters comprise a first optimal inspection wavelength band selected from wavelengths in an opaque regime defined by wavelengths shorter than the opacity transition wavelength and a second optimal inspection wavelength band selected from wavelengths in a transmissive regime defined by wavelengths longer than the opacity transition wavelength.

16. The method of claim 15, wherein the inspection comprises illuminating the specimen with selected wavelengths of light that comprise the first optimal inspection wavelength band, the second optimal inspection wavelength band, or both the first optimal inspection wavelength band and the second optimal inspection wavelength band.

* * * * *